US011221306B2

United States Patent
Lee et al.

(10) Patent No.: US 11,221,306 B2
(45) Date of Patent: Jan. 11, 2022

(54) GAS DETECTION COMPOSITE COMPRISING CEO2 UNIFORMLY LOADED ON OXIDE NANOSTRUCTURE AND METHOD OF PREPARATION THEREOF

(71) Applicant: Korea University Research and Business Foundation, Seoul (KR)

(72) Inventors: Jong Heun Lee, Seoul (KR); Jee-Uk Yoon, Zurich (CH); Jun-Sik Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 827 days.

(21) Appl. No.: 15/751,679

(22) PCT Filed: Aug. 10, 2016

(86) PCT No.: PCT/KR2016/008770
§ 371 (c)(1),
(2) Date: Feb. 9, 2018

(87) PCT Pub. No.: WO2017/026785
PCT Pub. Date: Feb. 16, 2017

(65) Prior Publication Data
US 2018/0231482 A1   Aug. 16, 2018

(30) Foreign Application Priority Data
Aug. 10, 2015   (KR) .................. 10-2015-0112273

(51) Int. Cl.
| G01N 27/00 | (2006.01) |
| G01N 27/12 | (2006.01) |
| G01N 33/497 | (2006.01) |
| C01F 17/235 | (2020.01) |
| C01G 9/02 | (2006.01) |
| C01G 15/00 | (2006.01) |
| C01G 19/02 | (2006.01) |
| C01G 41/02 | (2006.01) |
| C01G 53/04 | (2006.01) |
| B82Y 15/00 | (2011.01) |
| G01N 33/00 | (2006.01) |

(52) U.S. Cl.
CPC ........... *G01N 27/12* (2013.01); *C01F 17/235* (2020.01); *C01G 9/02* (2013.01); *C01G 15/00* (2013.01); *C01G 19/02* (2013.01); *C01G 41/02* (2013.01); *C01G 53/04* (2013.01); *G01N 27/127* (2013.01); *G01N 33/497* (2013.01); *B82Y 15/00* (2013.01); *G01N 33/006* (2013.01)

(58) Field of Classification Search
CPC .... G01N 33/497; G01N 27/12; G01N 27/127; C01F 17/235; C01G 9/02; C01G 15/00; C01G 19/02; C01G 41/02; C01G 53/04
See application file for complete search history.

(56) References Cited

U.S. PATENT DOCUMENTS

| 8,017,036 B1* | 9/2011 | Austin | B82Y 40/00 |
| | | | 252/301.4 R |
| 2004/0009109 A1* | 1/2004 | Akimoto | C01G 1/02 |
| | | | 423/263 |
| 2006/0229197 A1* | 10/2006 | Stark | C04B 35/6264 |
| | | | 502/304 |
| 2007/0042526 A1* | 2/2007 | Myeong | A61K 8/044 |
| | | | 438/104 |
| 2007/0149395 A1* | 6/2007 | Kroell | A61K 8/27 |
| | | | 502/304 |
| 2016/0178804 A1* | 6/2016 | Shen | C01G 39/02 |
| | | | 252/587 |

FOREIGN PATENT DOCUMENTS

| KR | 2004-0100136 | * 12/2004 |
| KR | 101400605 B1 | 5/2014 |
| KR | 20150051249 A | 5/2015 |
| KR | 20150085560 A | 7/2015 |
| KR | 20150139245 A | 12/2015 |
| KR | 10194734 B1 | 2/2016 |
| WO | 2015-018328 | * 2/2015 |

OTHER PUBLICATIONS

Gerasimov et al., "Sensor Properties of the Nanostructured In2O3-CeO2 System in Detection of Reducing Gases," Russian Journal of Physical Chemistry A. (2014); 88(3):503-508.
Kim et al., "Design of Selective Gas Sensors Using Additive-Loaded In2O3 Hllow Spheres Preparped by Combinatorial Hydrothermal Reactions," Sensors (Nov. 7, 2011); 11:10603-10614.
Kim et al., "The Role of NiO Doping in Reducing the Impact of Humidity on the Performance of SnO2-Based Gas Sensors: Synthesis Strategies, and Phenomenological and Spectroscopic Studies," Adv. Funct. Mater. (2011); 21:4456-4463.

* cited by examiner

*Primary Examiner* — Steven J Bos
(74) *Attorney, Agent, or Firm* — Fox Rothschild LLP

(57) ABSTRACT

The present invention relates to a composite having the ability to stably and reliably detect a target gas even in a moist environment. The composite of the present invention includes: a nanostructure of an oxide semiconductor selected from the group consisting of $SnO_2$, ZnO, $WO_3$, NiO, and $In_2O_3$; and a $CeO_2$ additive loaded on the nanostructure. The oxide semiconductor nanostructure is uniformly loaded with $CeO_2$. The composite of the present invention can rapidly detect an analyte gas with high gas response irrespective of the presence and concentration of moisture. The present invention also relates to methods for preparing the composite, a gas sensor including the composite as a material for a gas sensing layer, and a method for fabricating the gas sensor.

6 Claims, 39 Drawing Sheets

[Fig. 1]
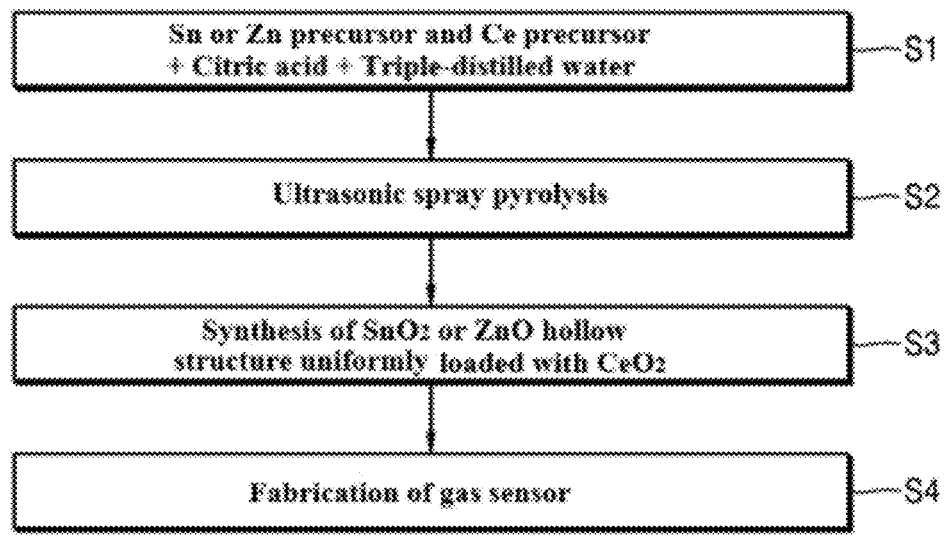
[Fig. 2]
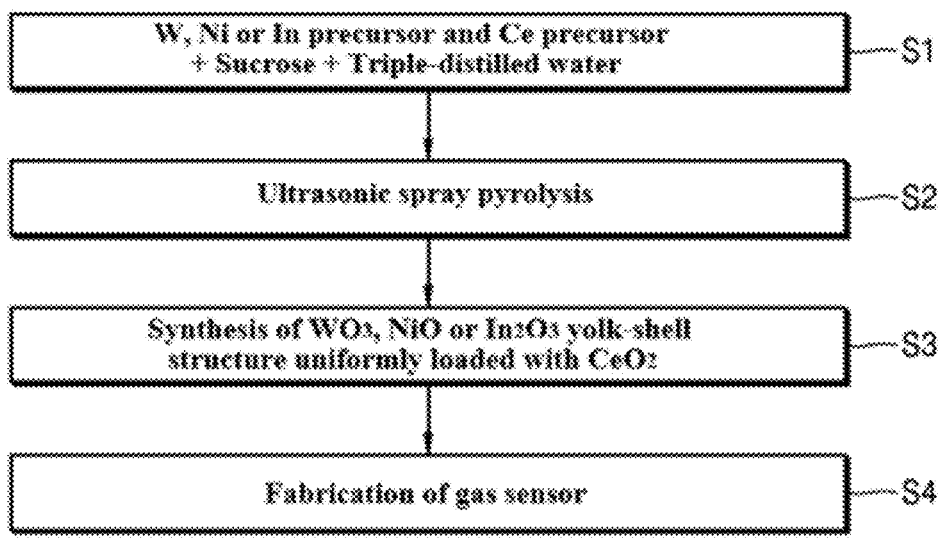

[Fig. 3]
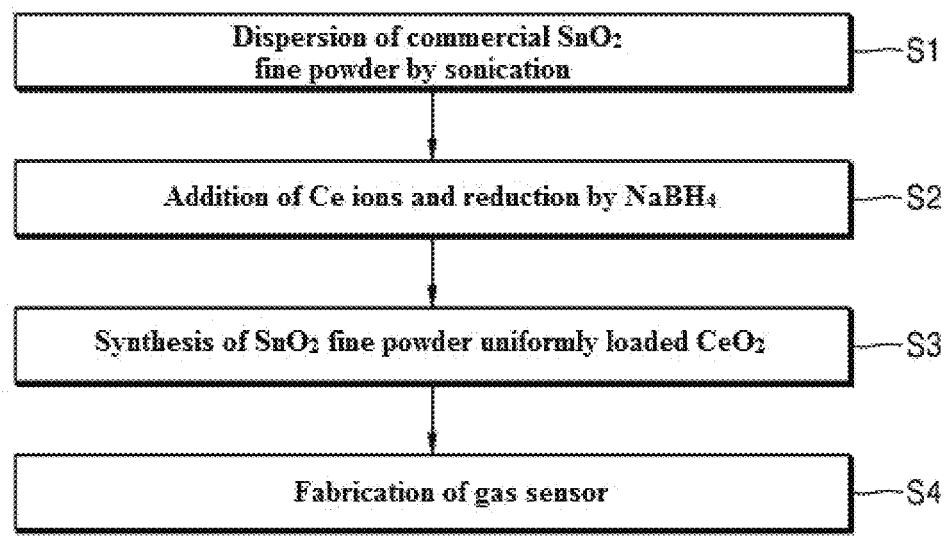

[Fig. 4]
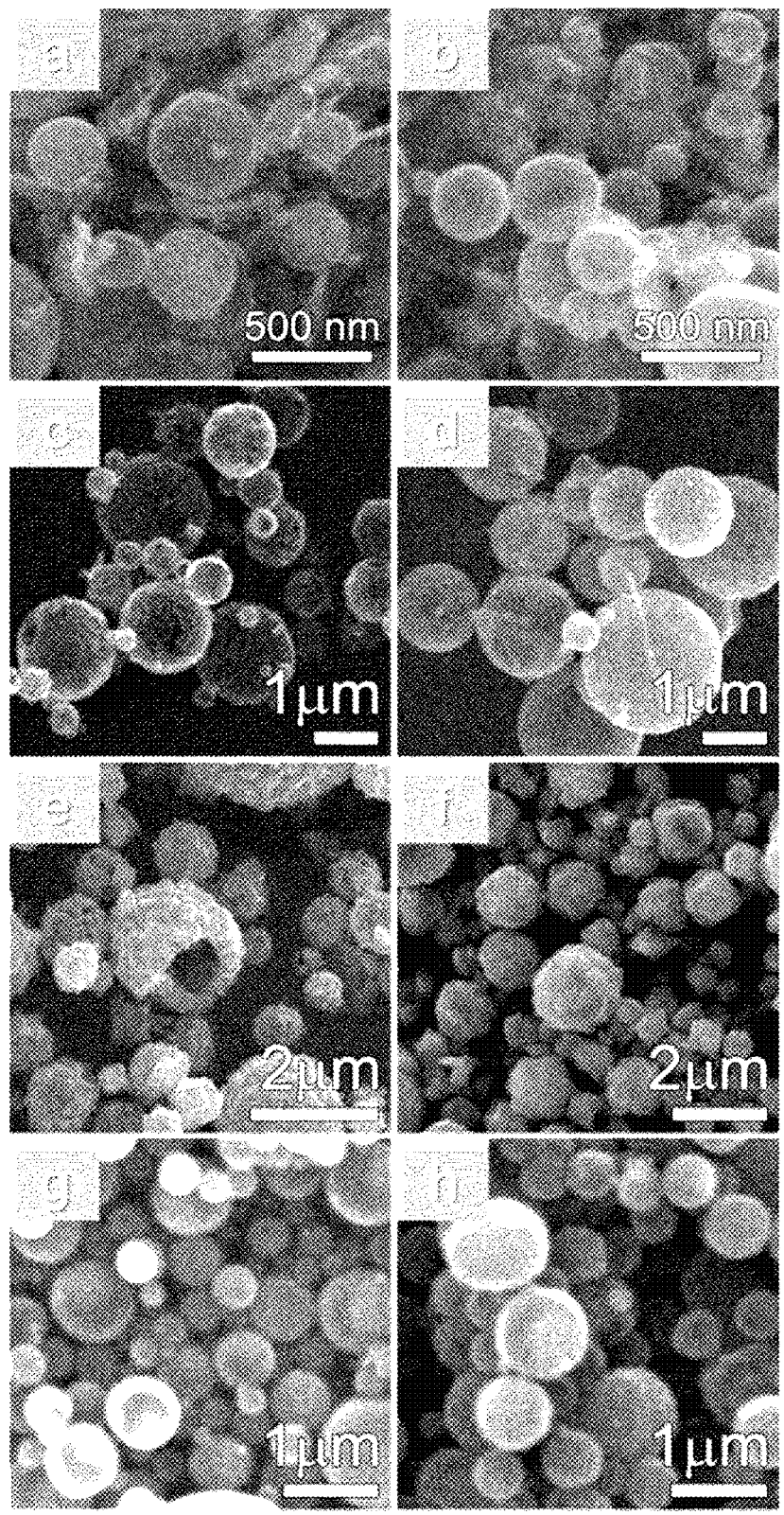

[Fig. 5]
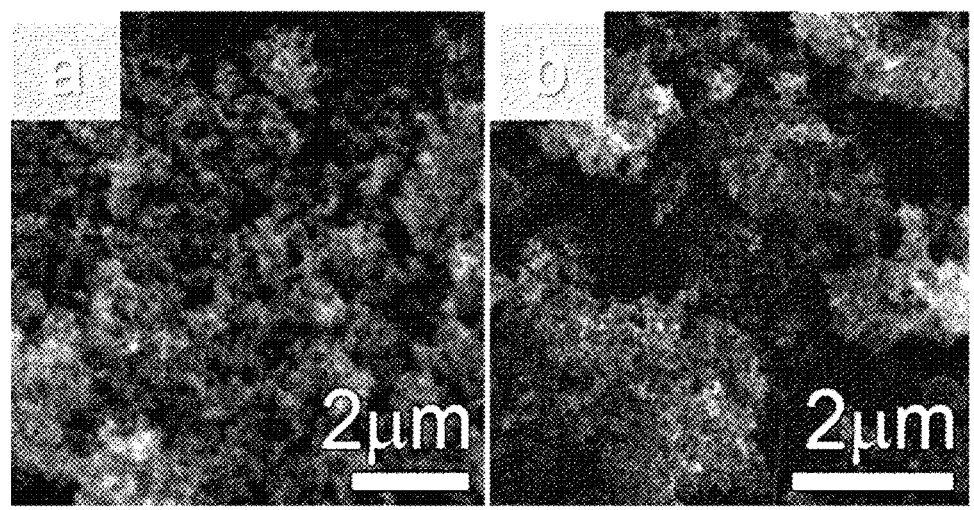
[Fig. 6]
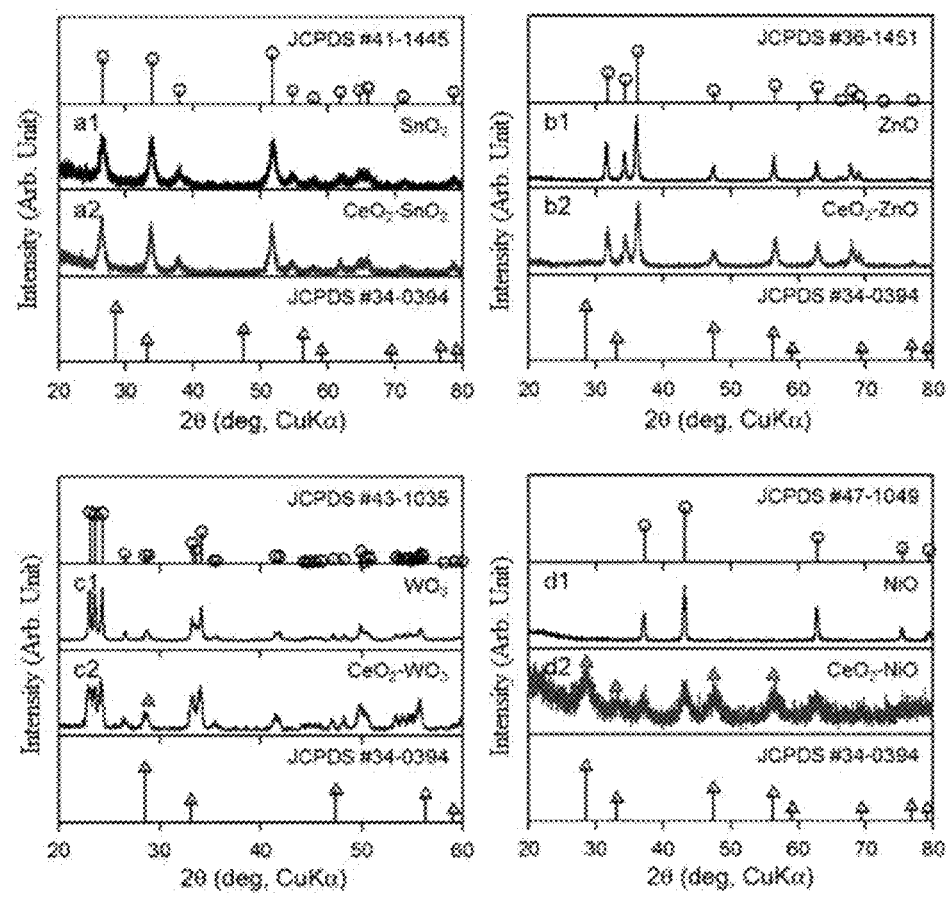

[Fig. 7]
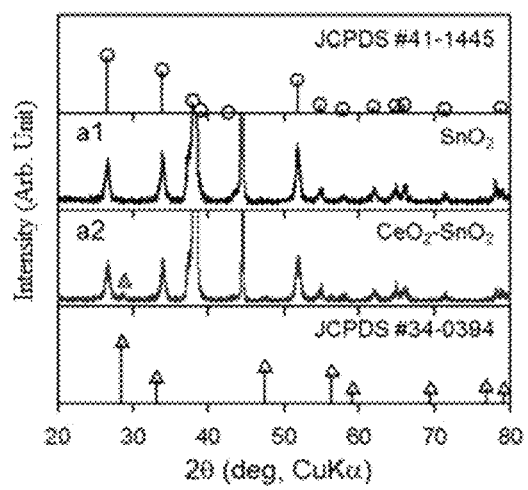

[Fig. 8]
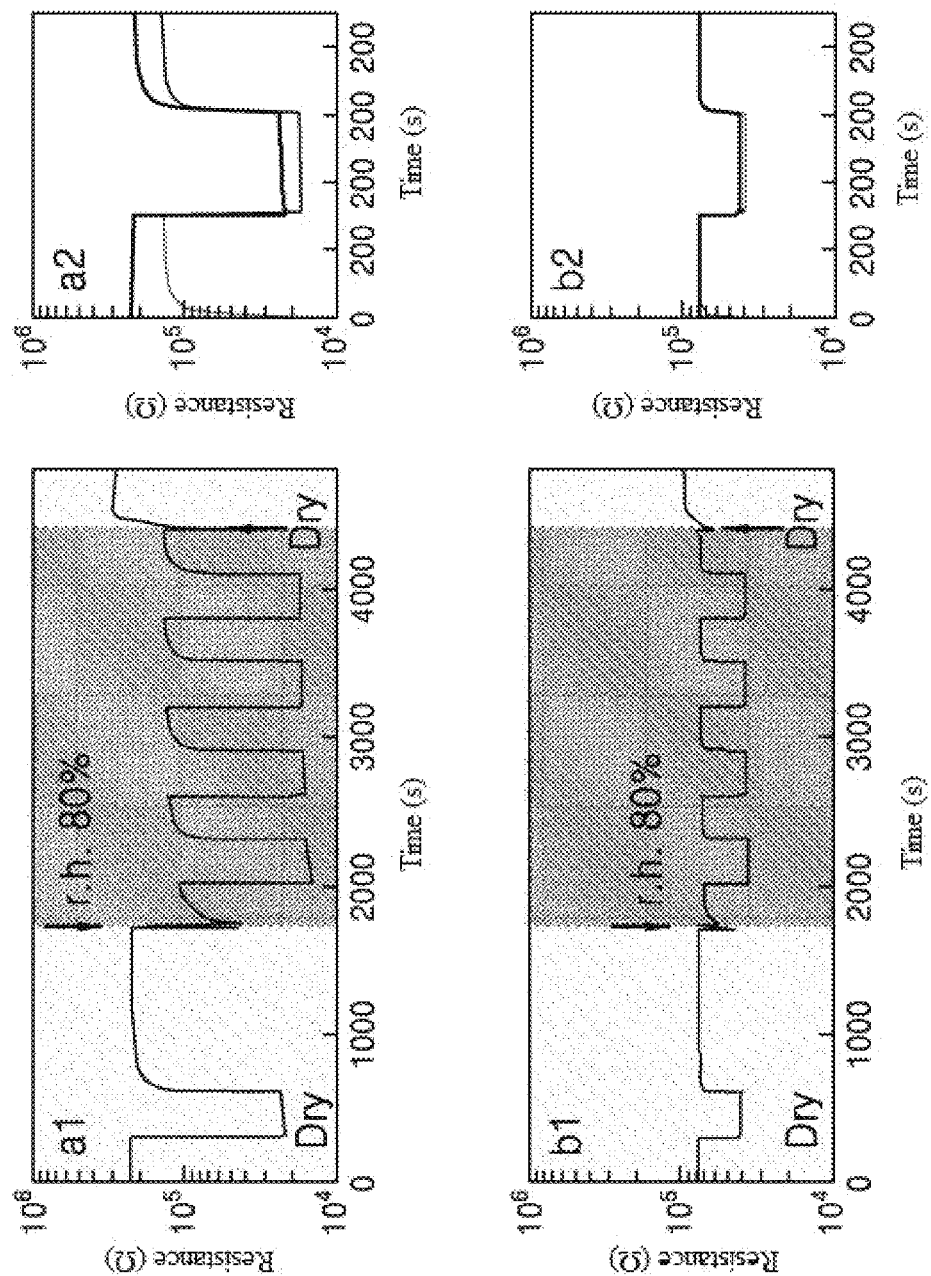

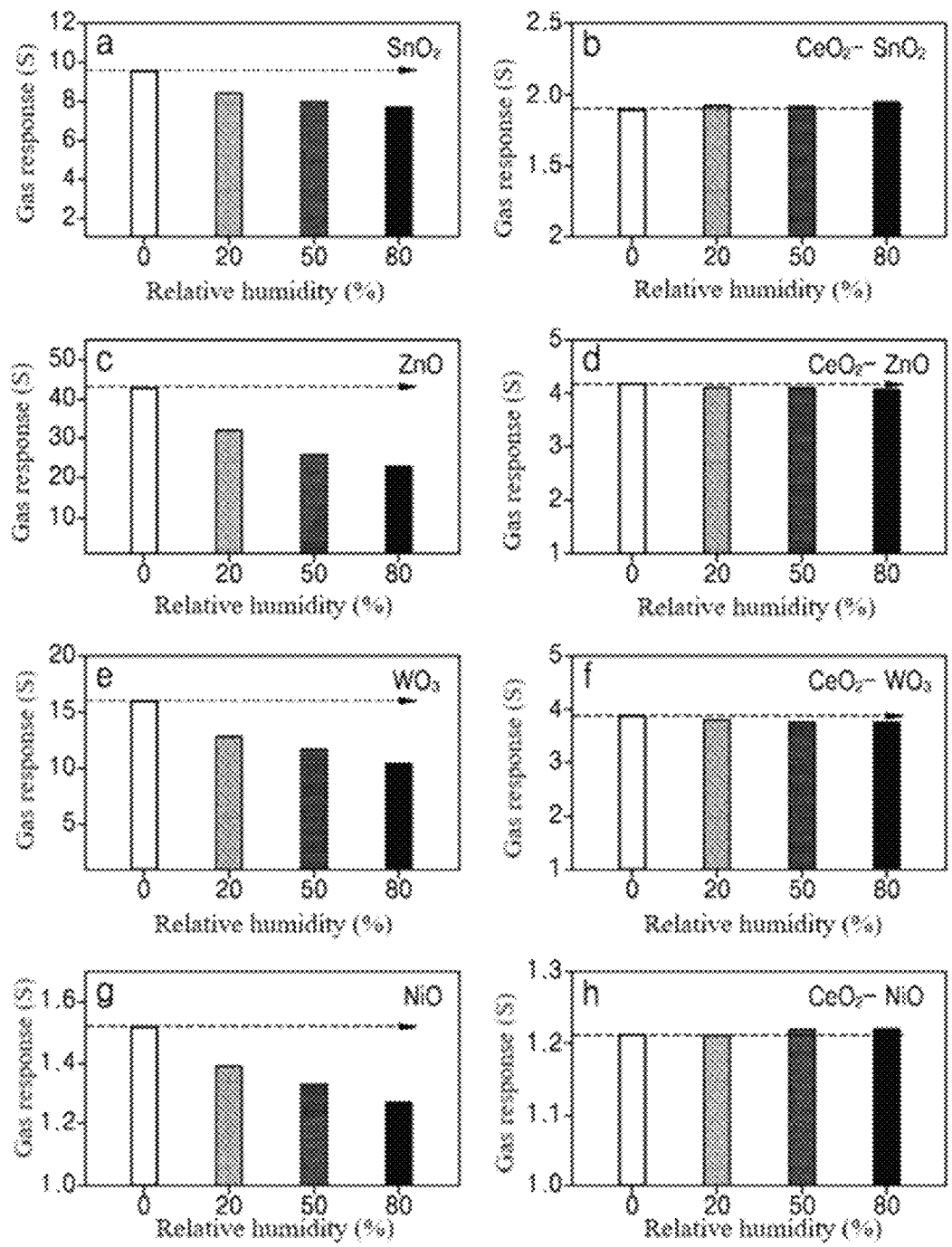
[Fig. 9]

[Fig. 10]
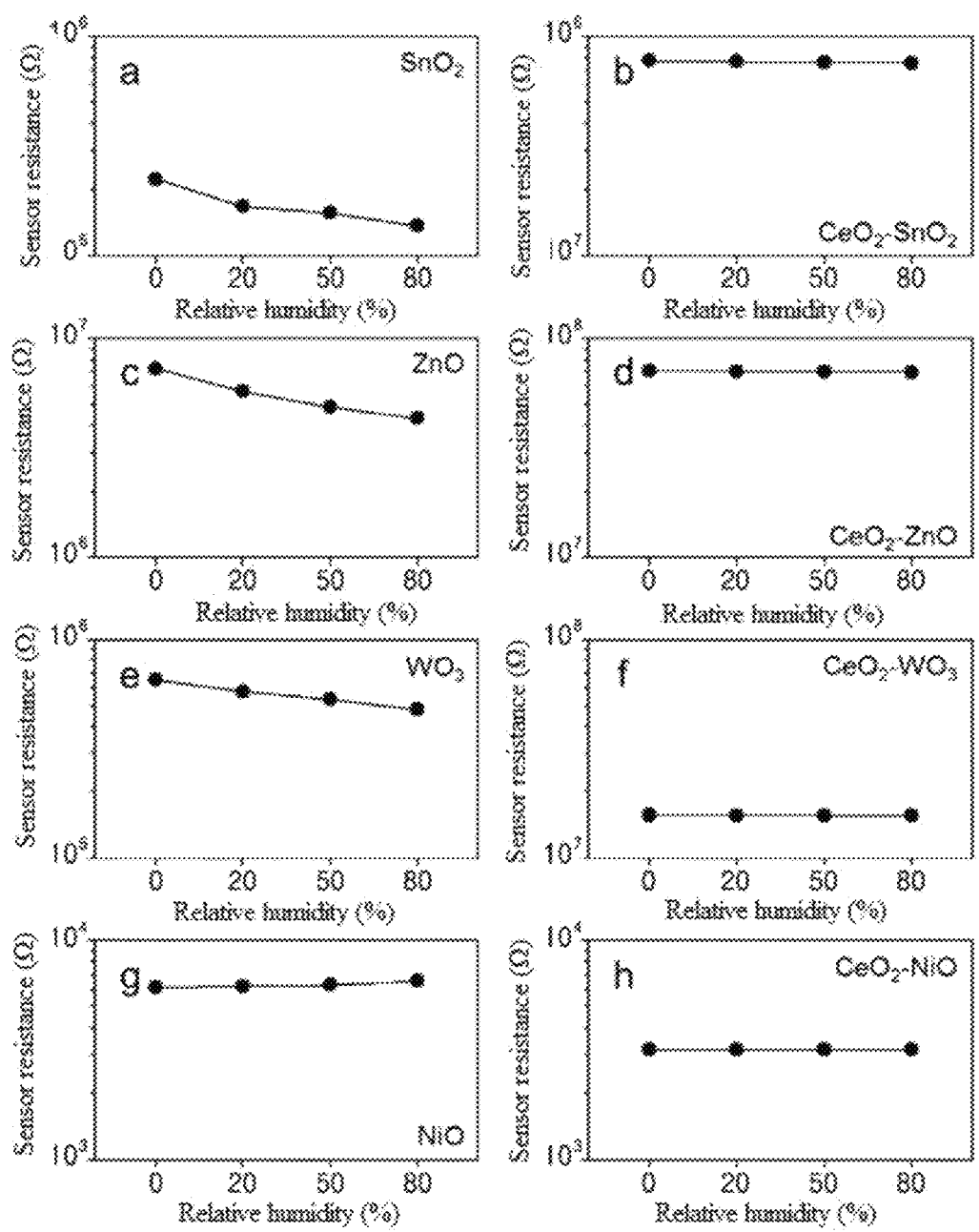

[Fig. 11]
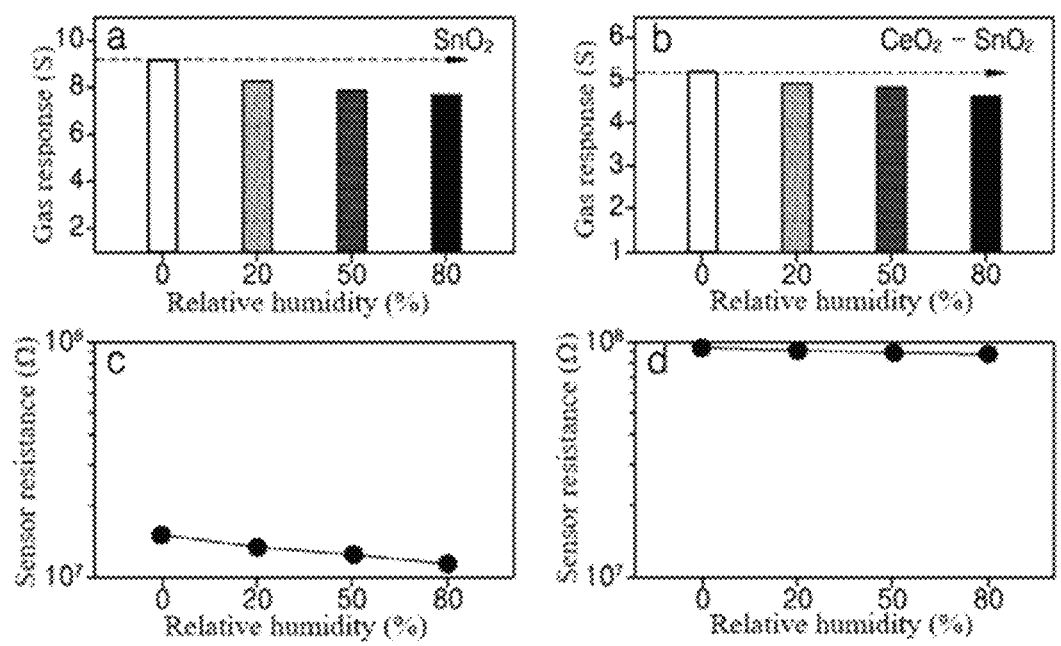

[Fig. 12]
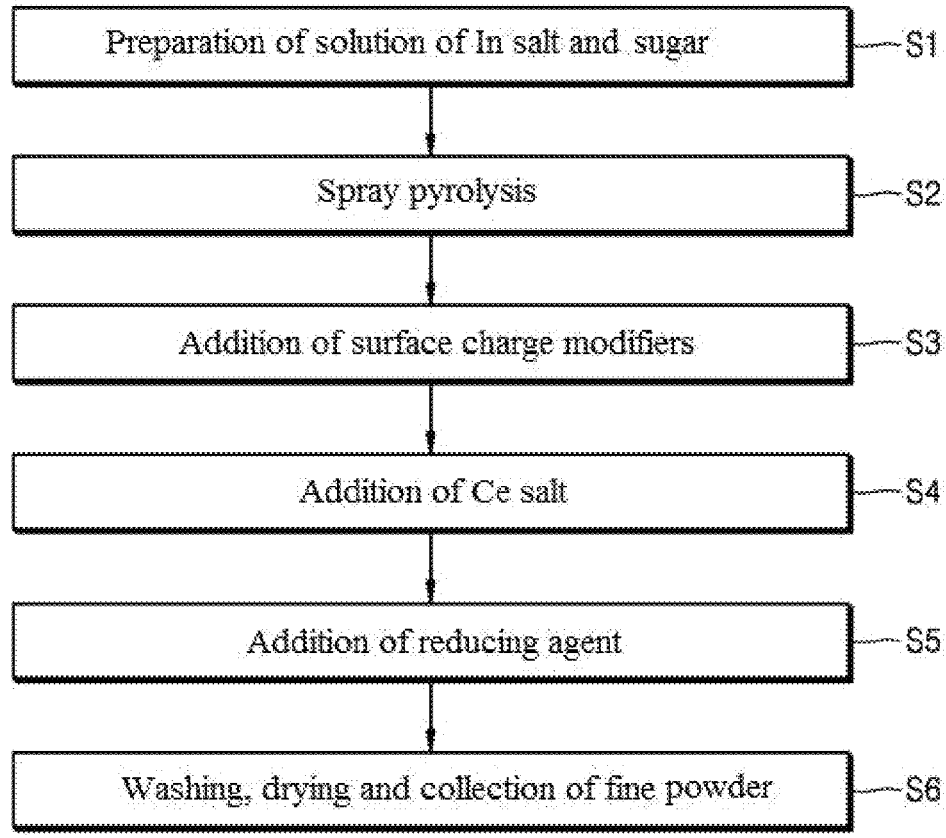
[Fig. 13]
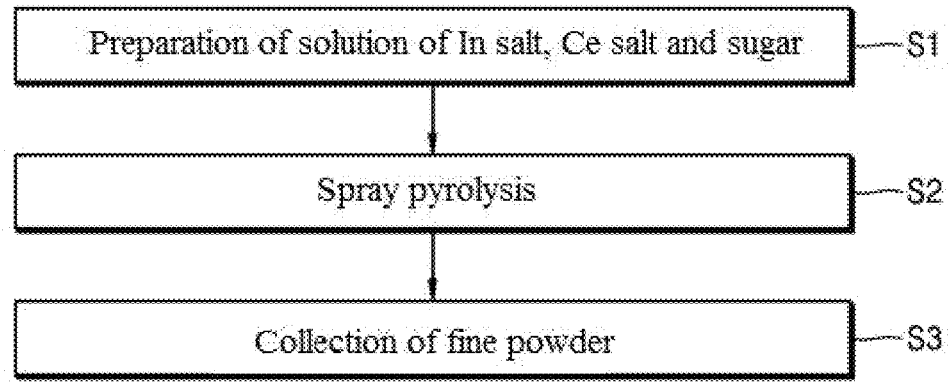

[Fig. 14a]
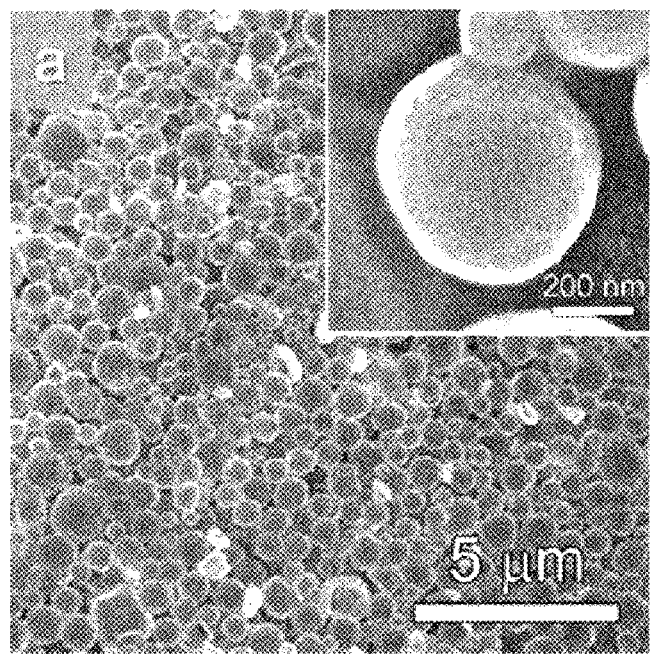
[Fig. 14b]
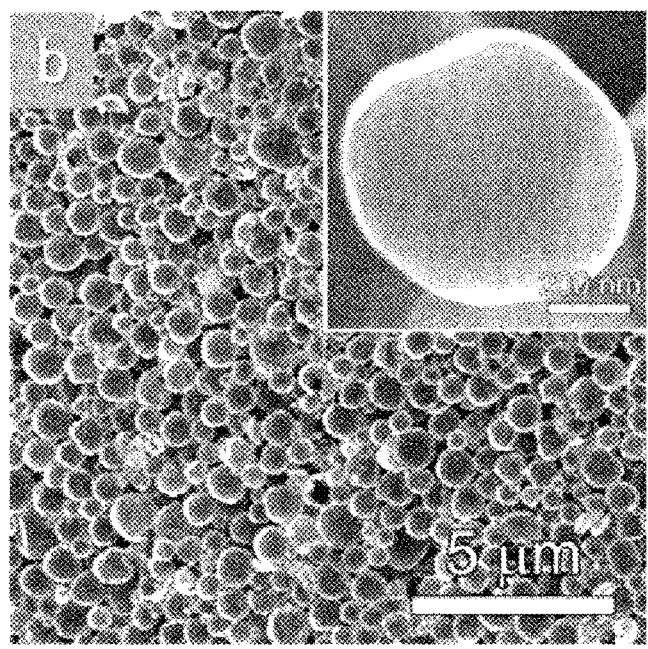

[Fig. 14c]
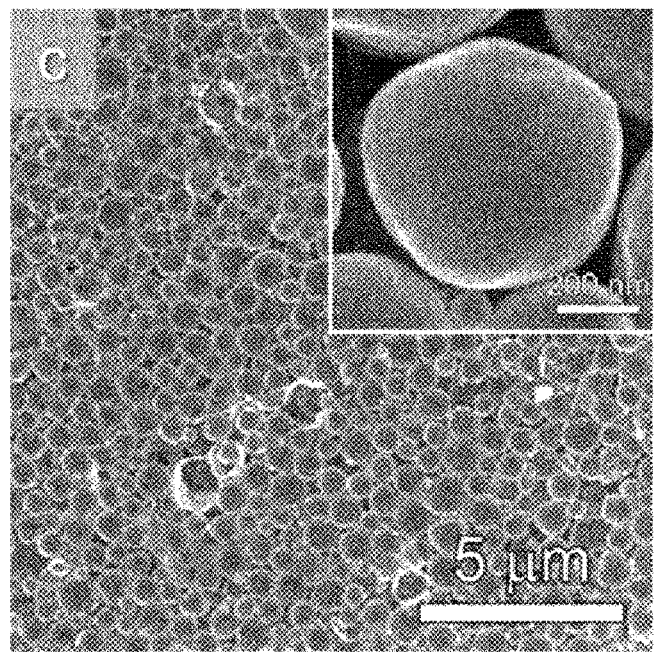
[Fig. 14d]
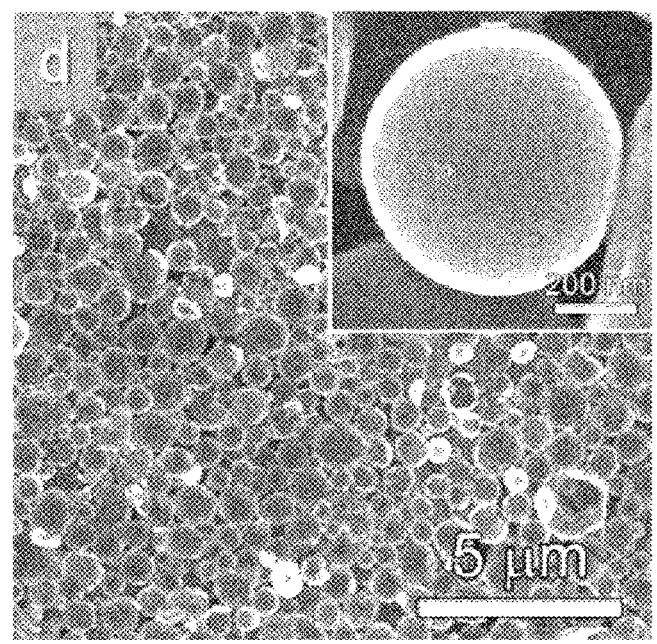

[Fig. 14e]
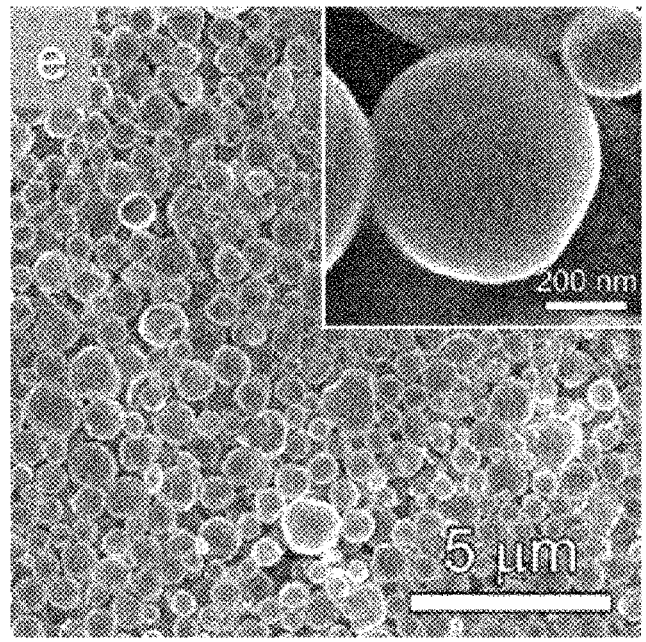
[Fig. 14f]
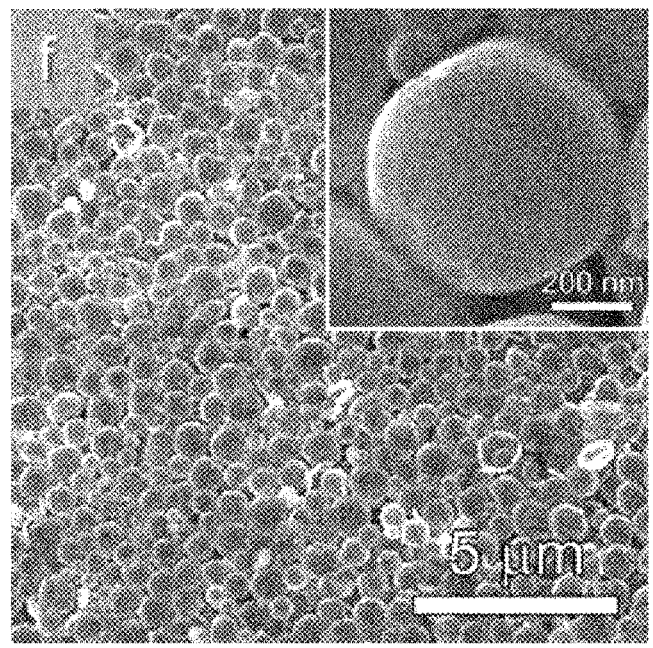

[Fig. 14g]
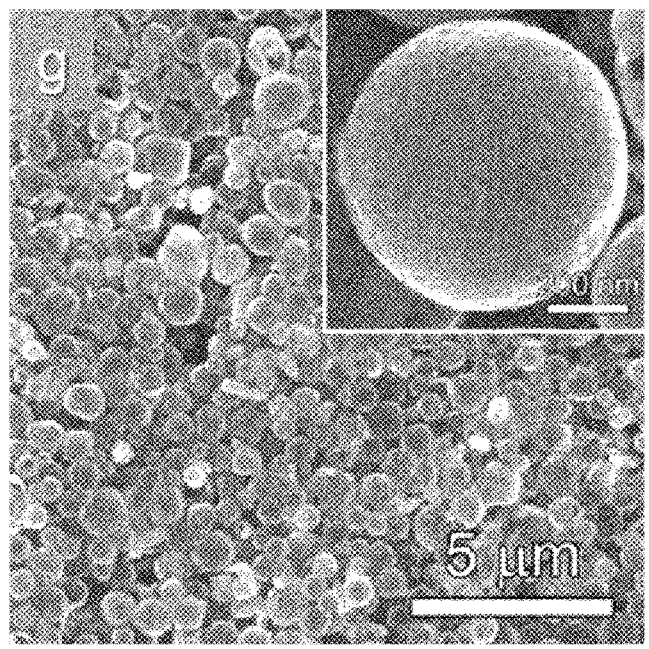
[Fig. 14h]
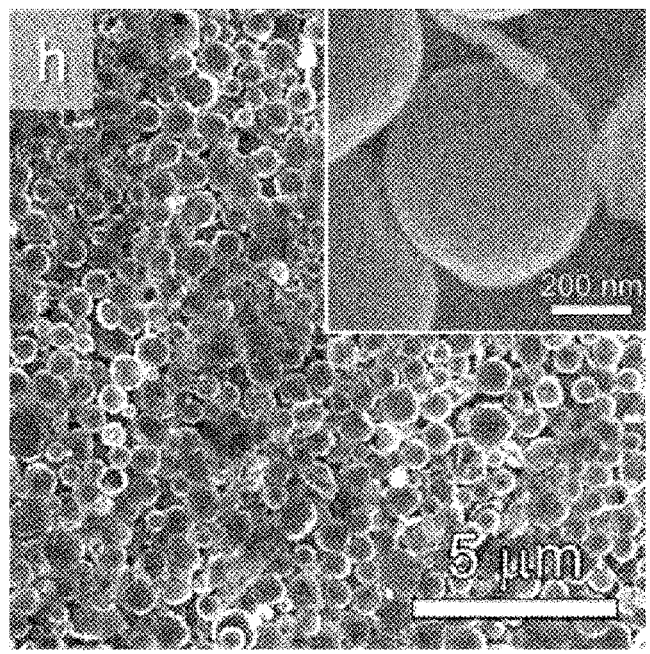

[Fig. 14i]
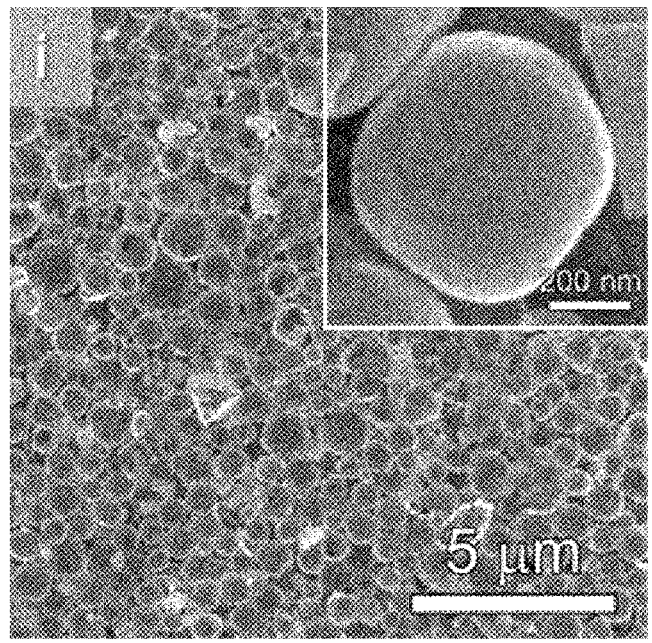
[Fig. 15a]
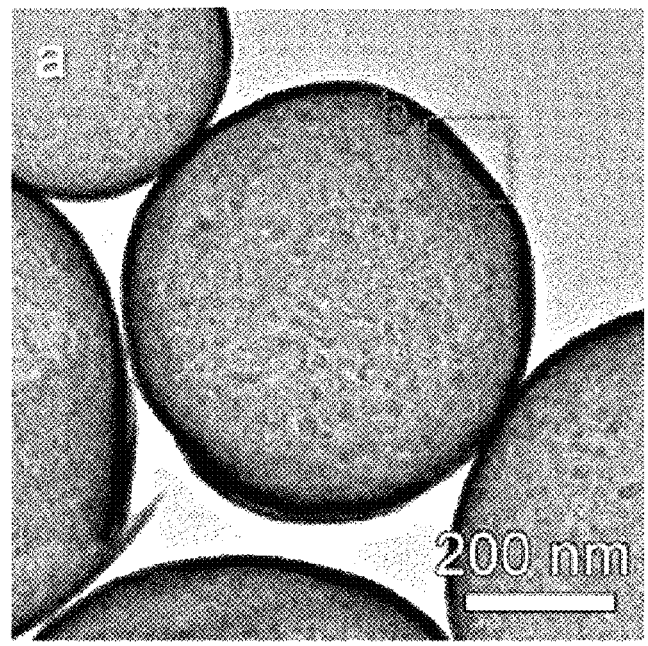

[Fig. 15b]
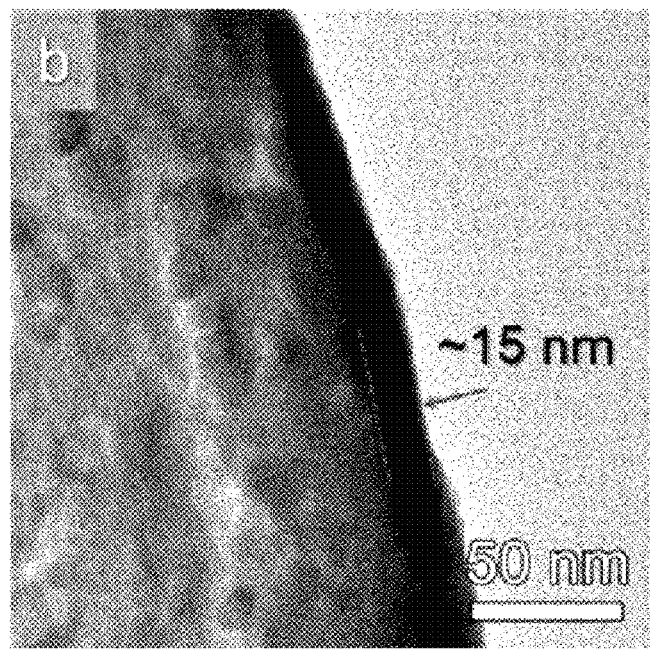
[Fig. 15c]
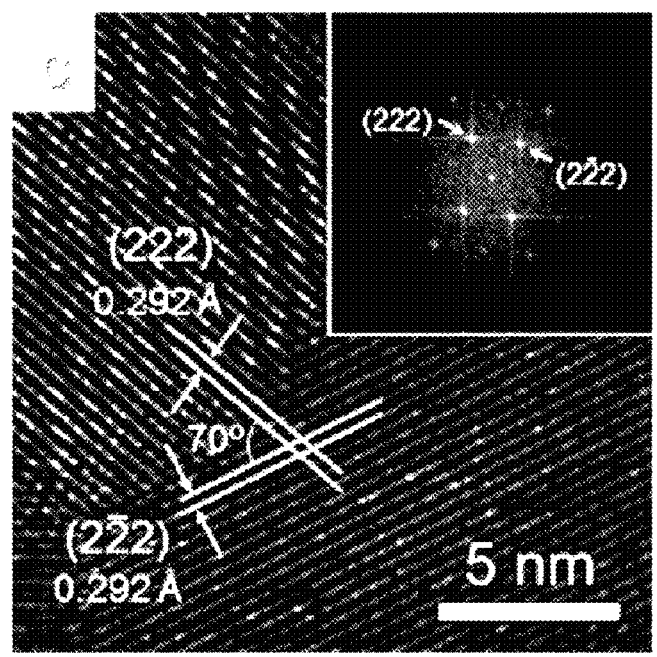

[Fig. 15d]
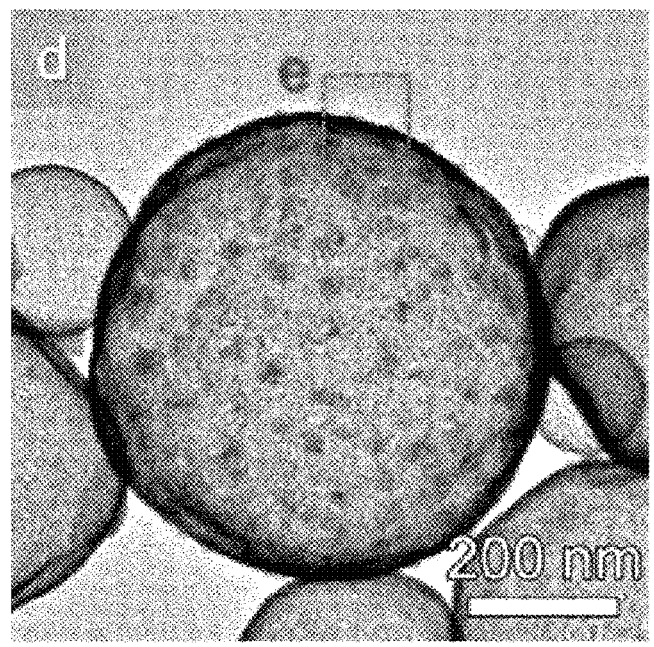
[Fig. 15e]
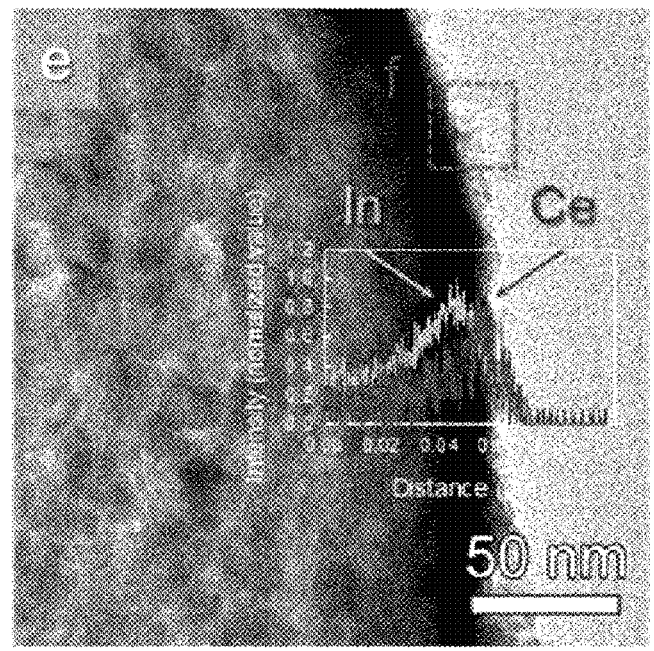

[Fig. 15f]
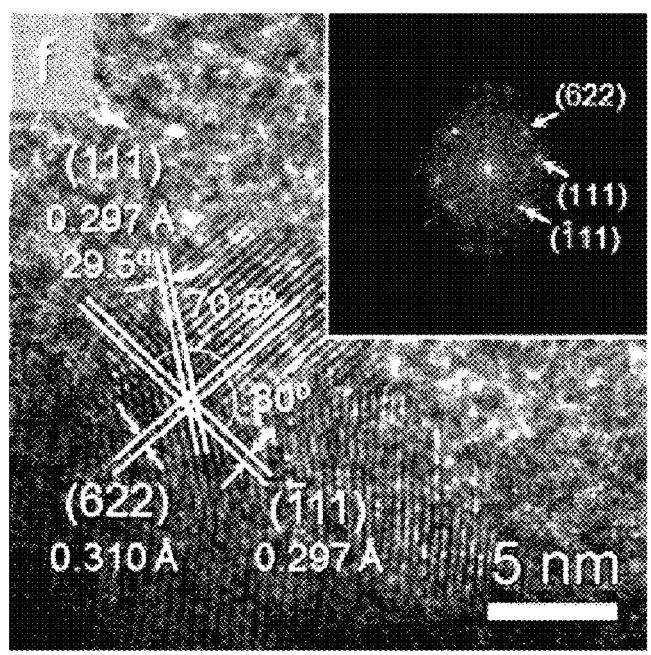
[Fig. 15g]
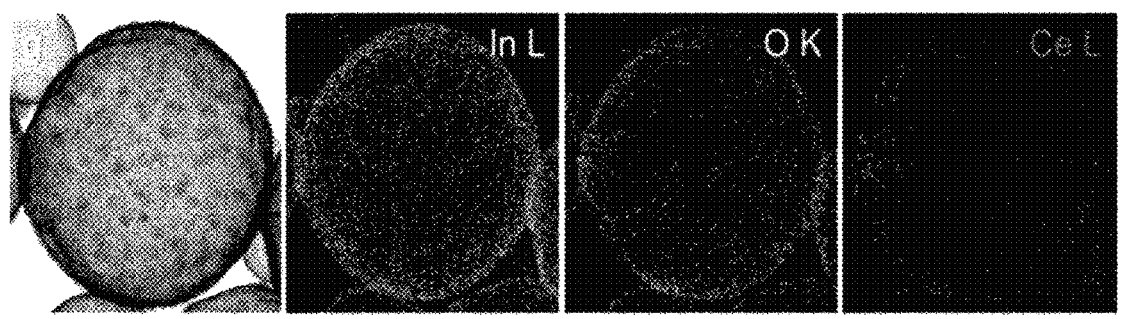

[Fig. 16a]
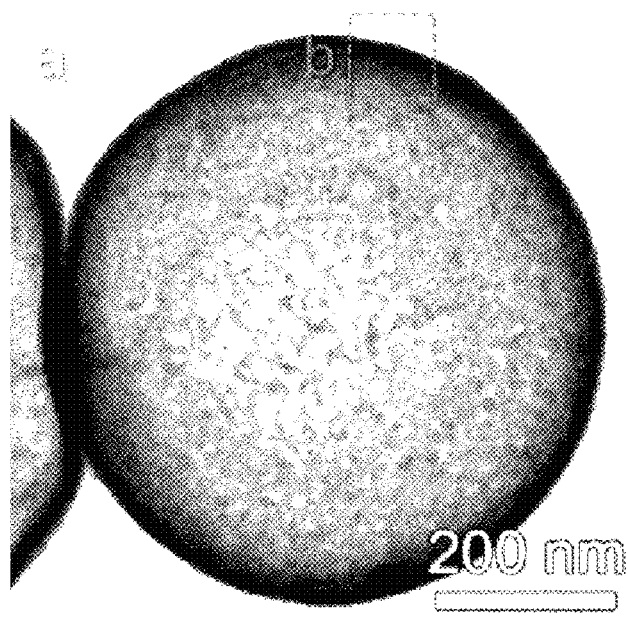
[Fig. 16b]
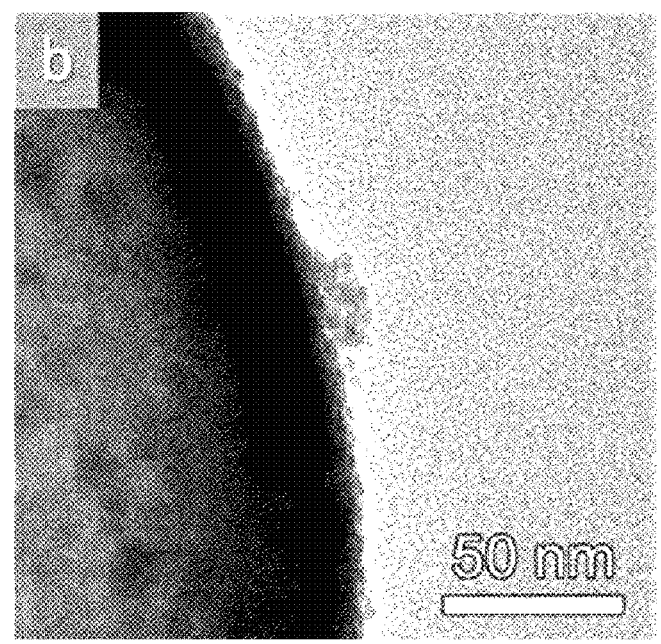

[Fig. 16c]
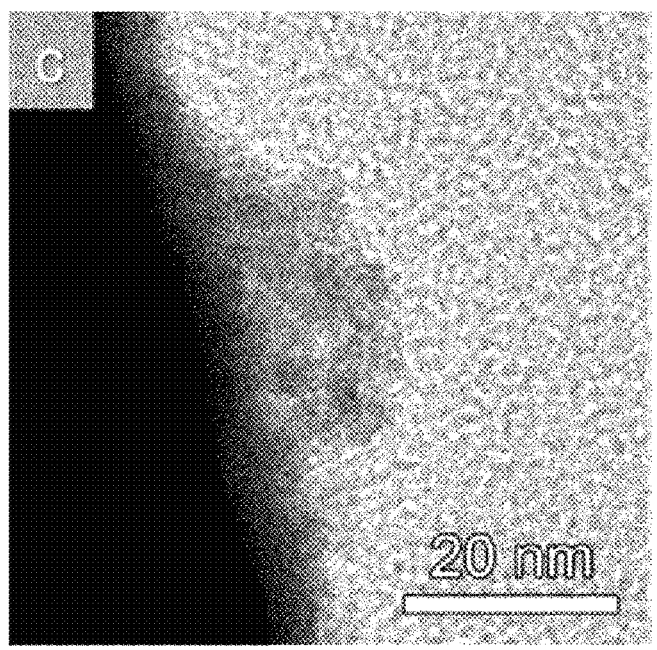
[Fig. 16d]
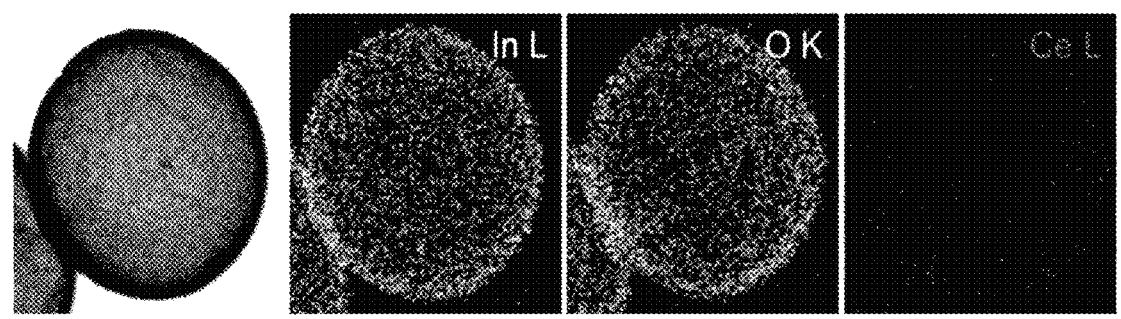

[Fig. 16e]
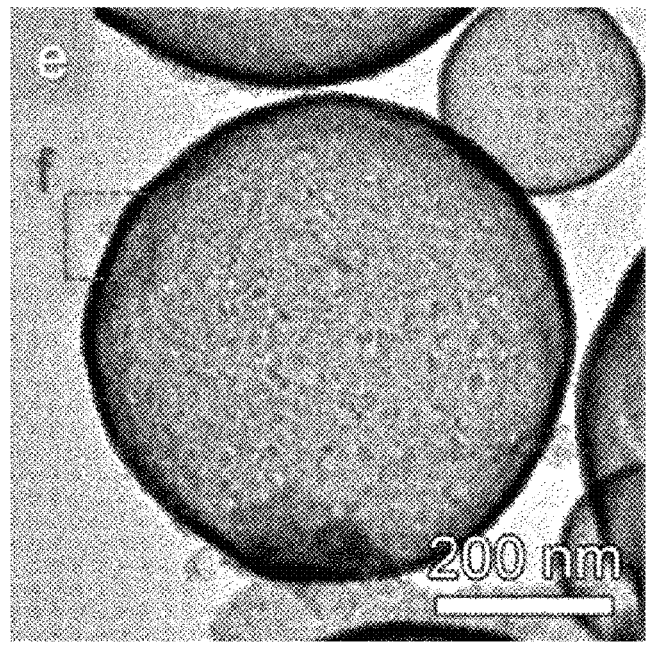
[Fig. 16f]
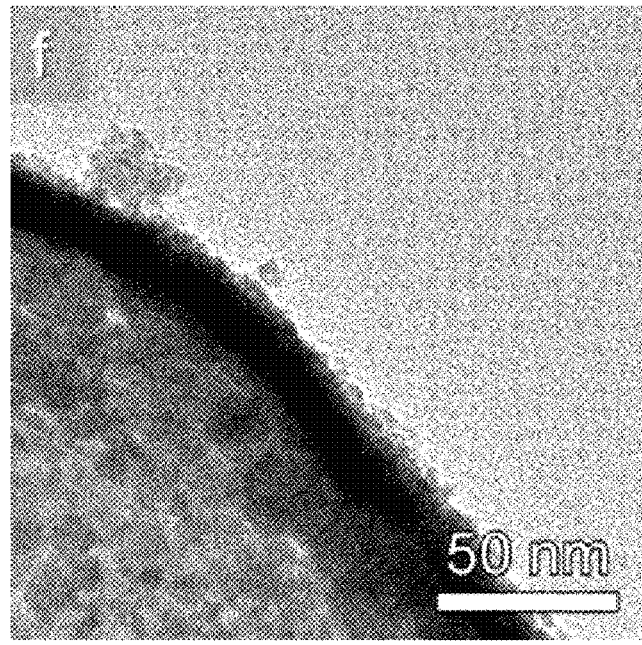

[Fig. 16g]
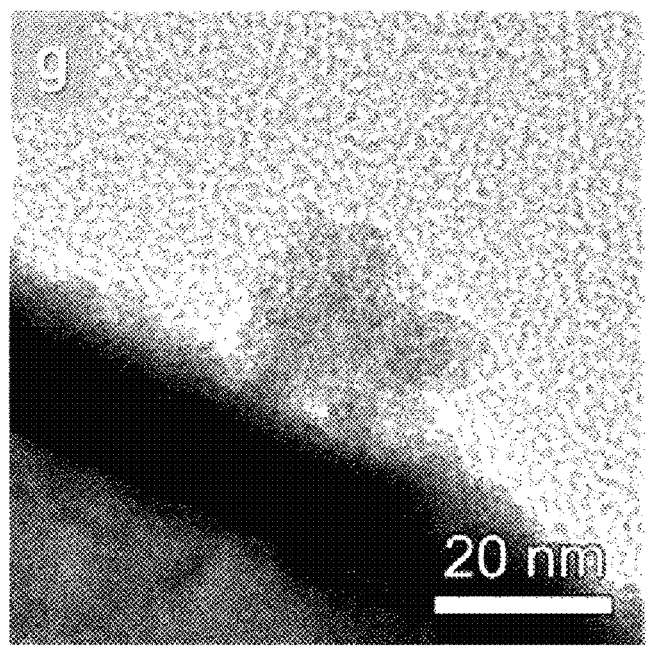
[Fig. 16h]
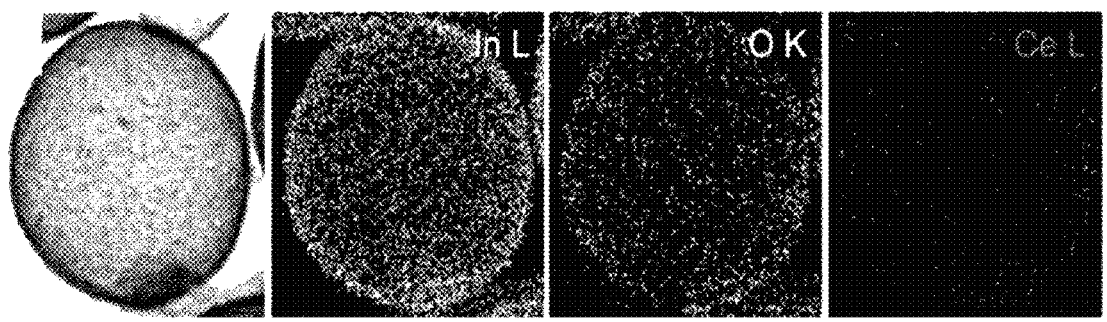

[Fig. 17a]
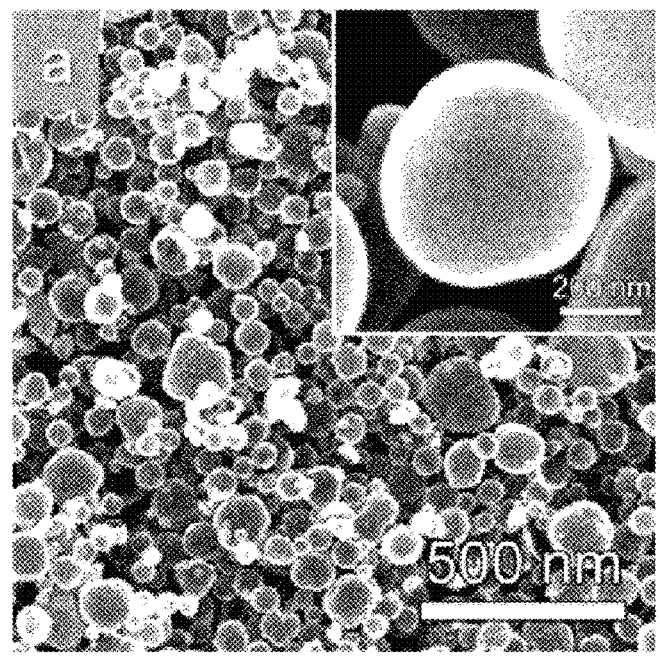
[Fig. 17b]
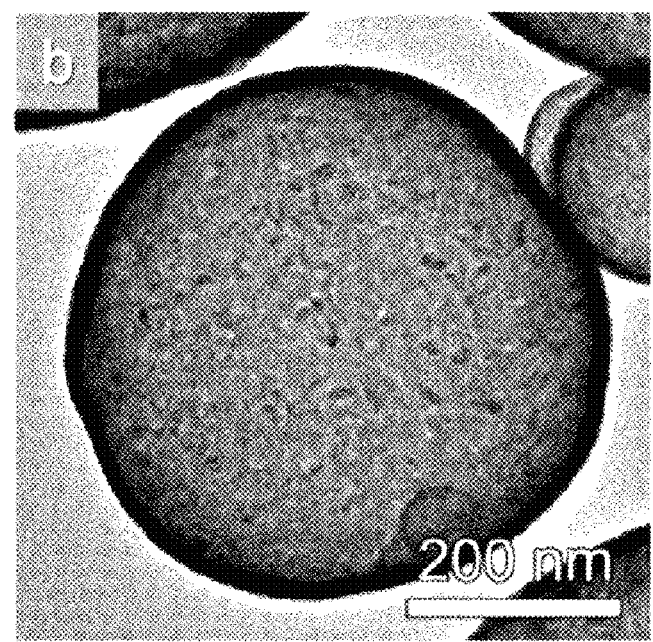

[Fig. 17c]
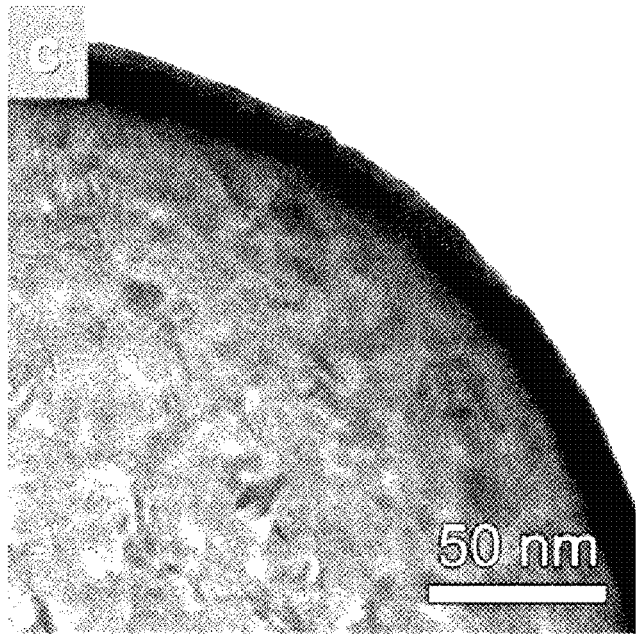
[Fig. 17d]
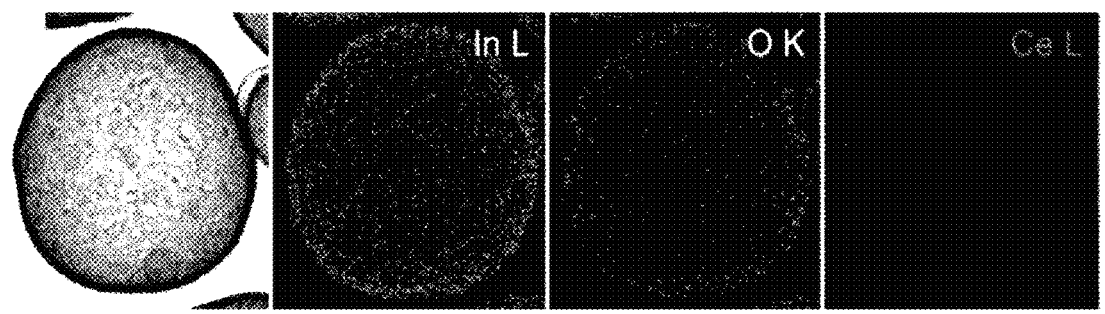

[Fig. 18]
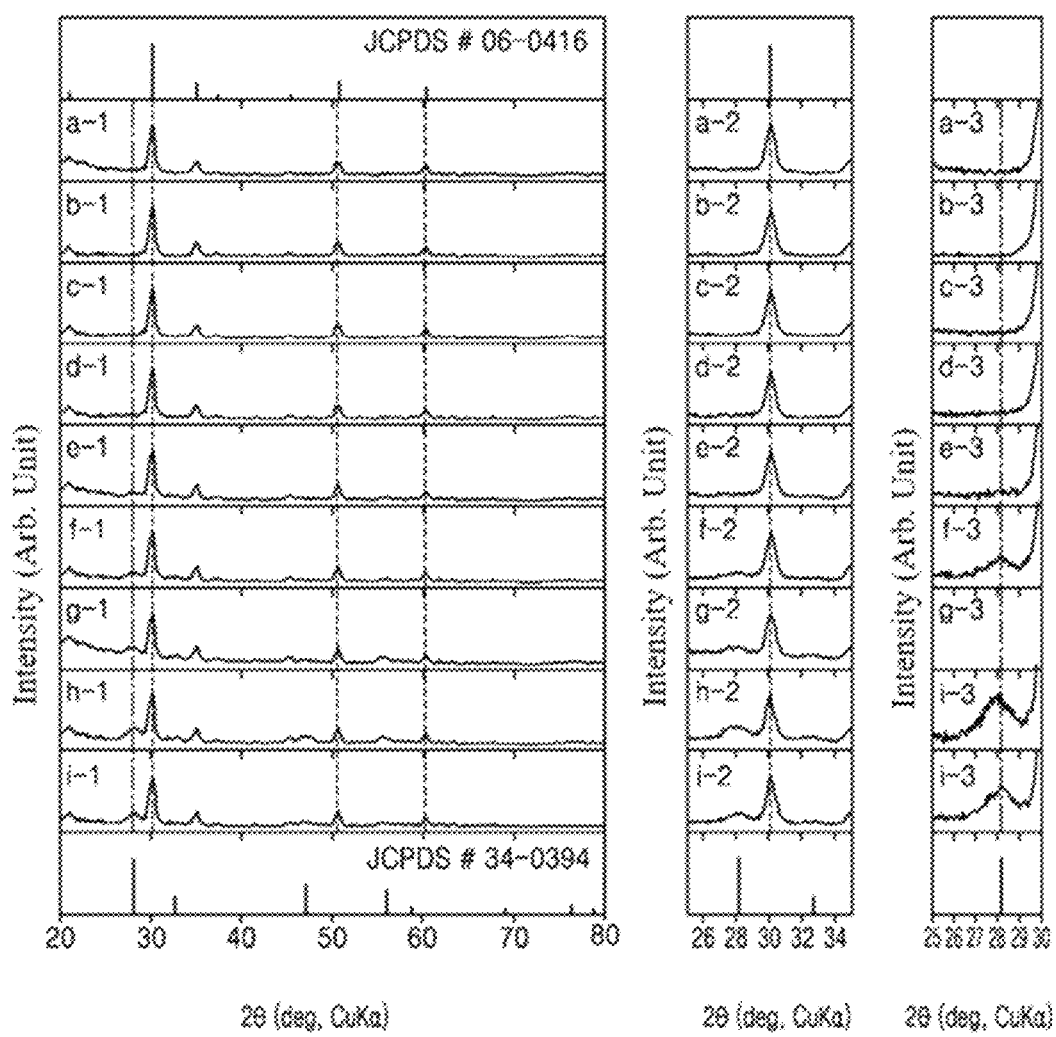

[Fig. 19]
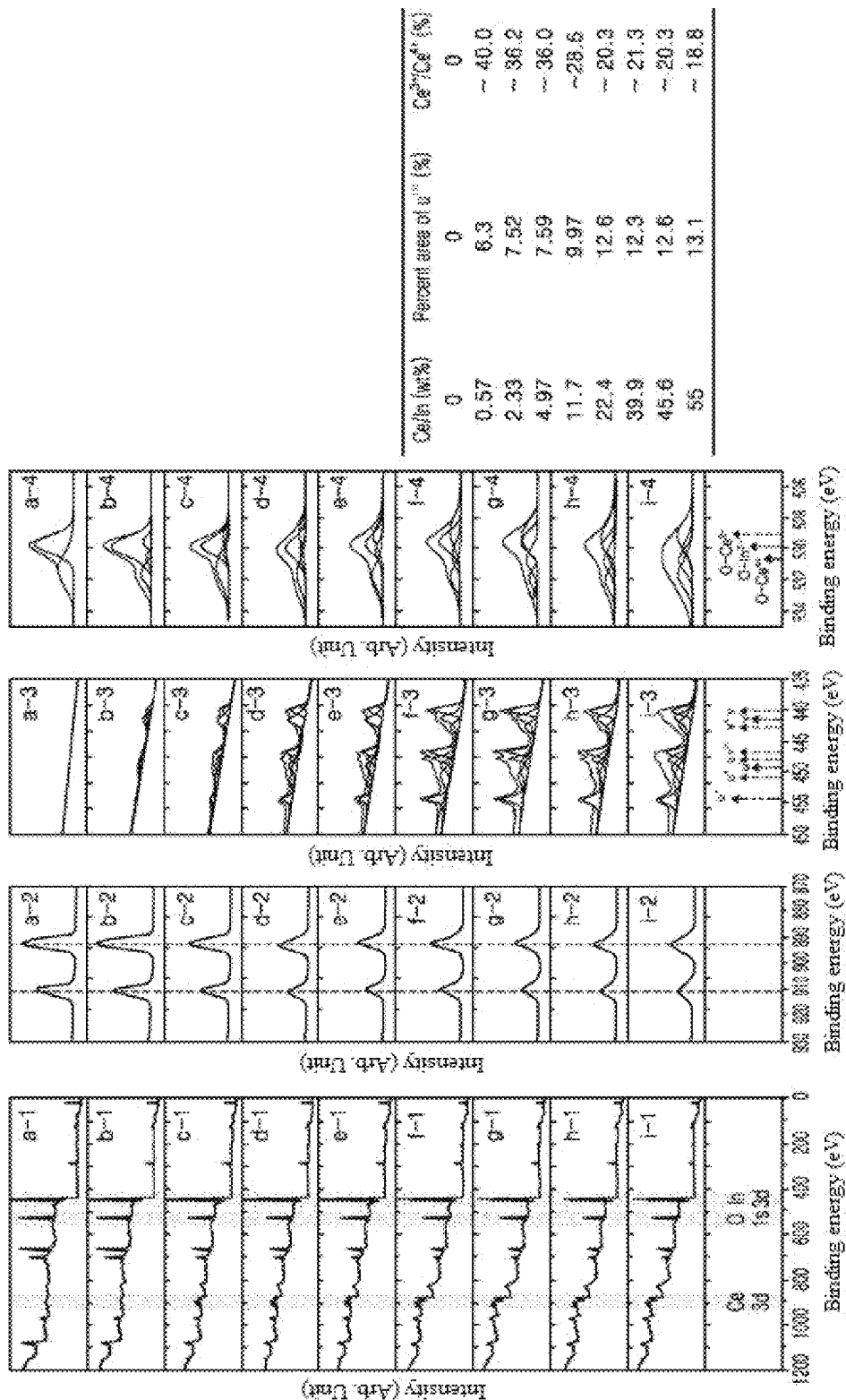

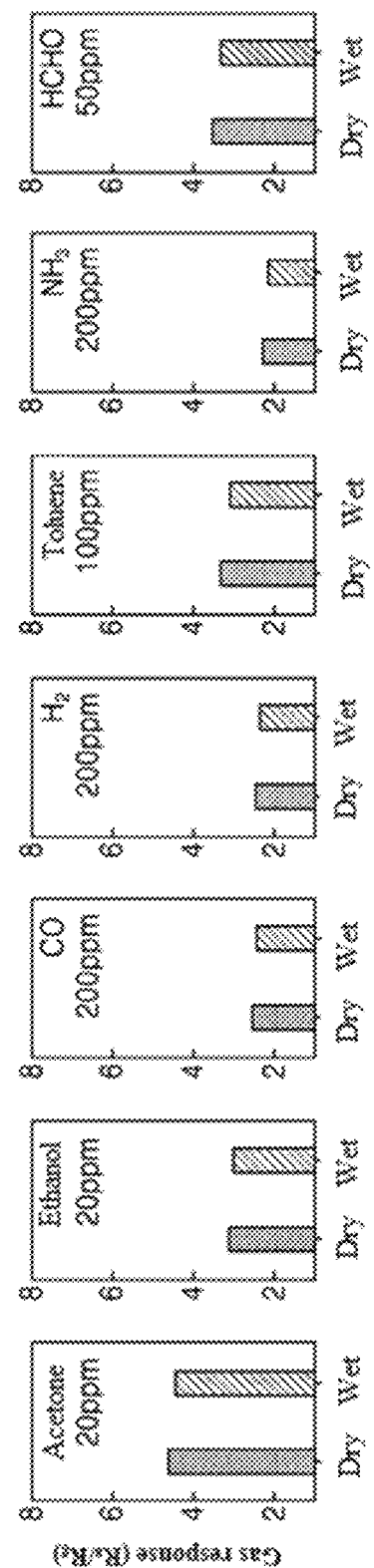
[Fig. 20a]

[Fig. 20b]
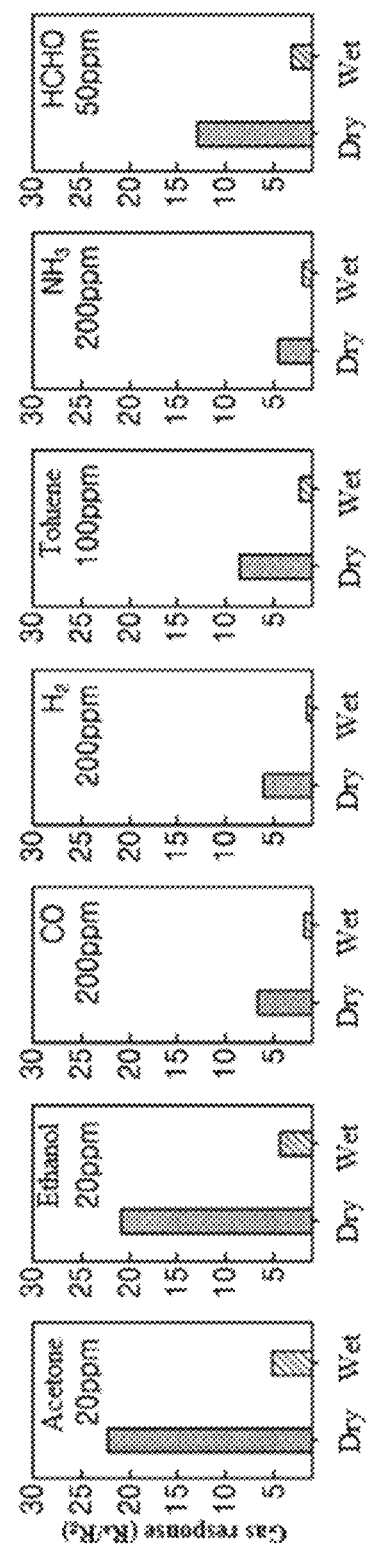

[Fig. 21a]
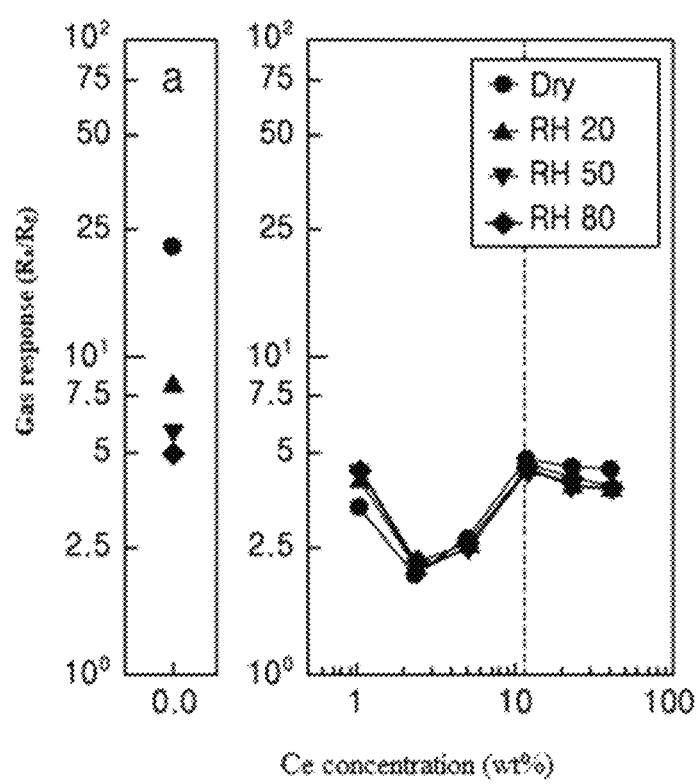

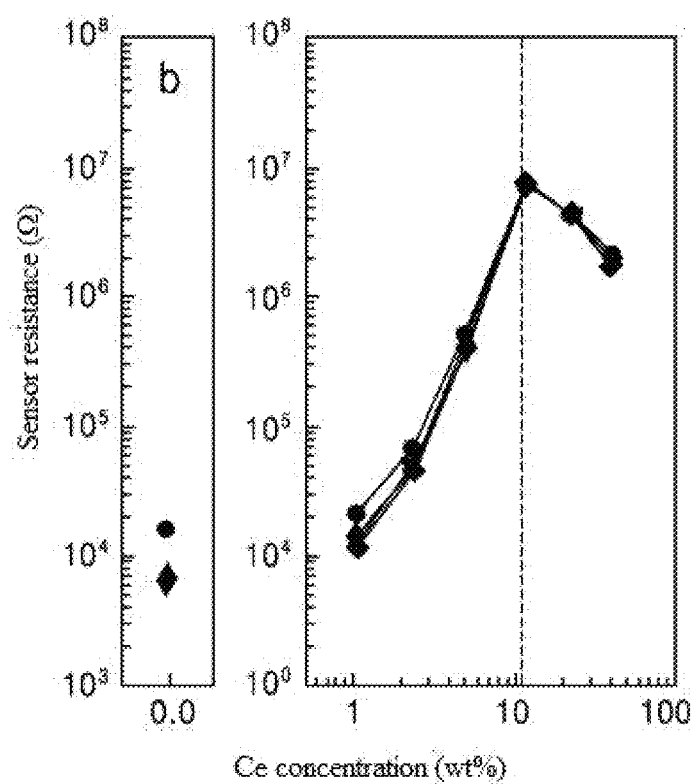
[Fig. 21b]

[Fig. 21c]
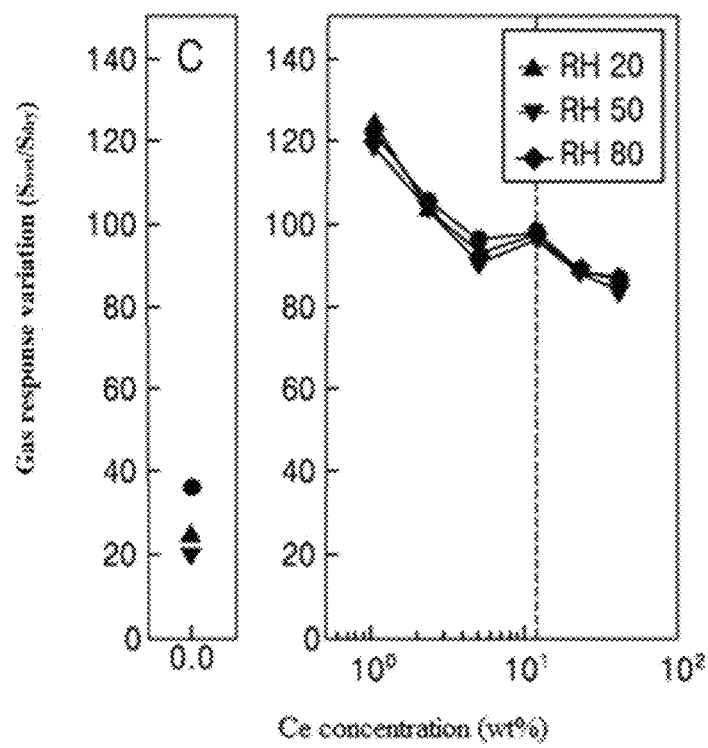
[Fig. 21d]
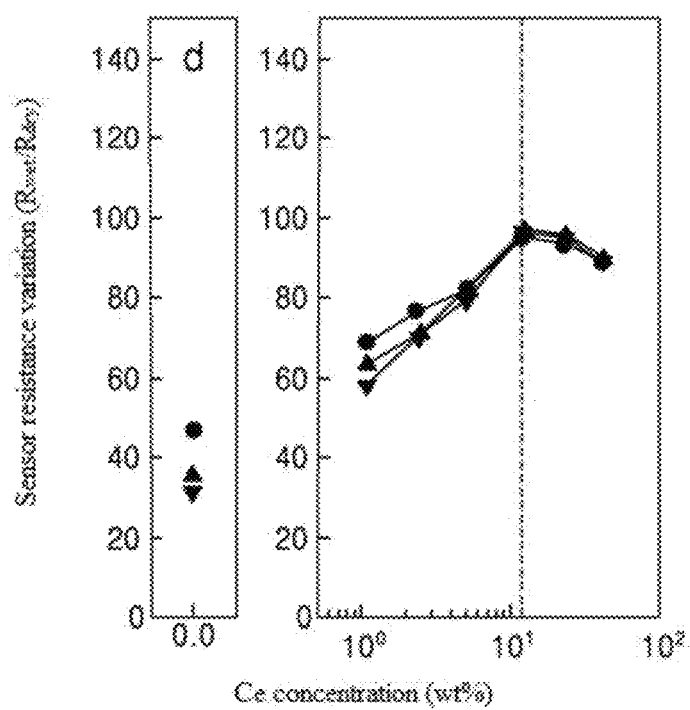

[Fig. 22a]
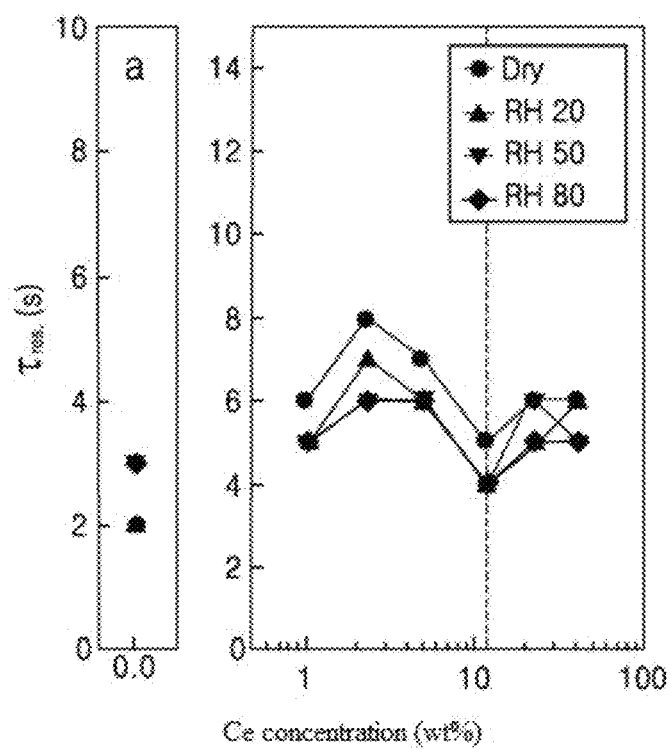

[Fig. 22b]
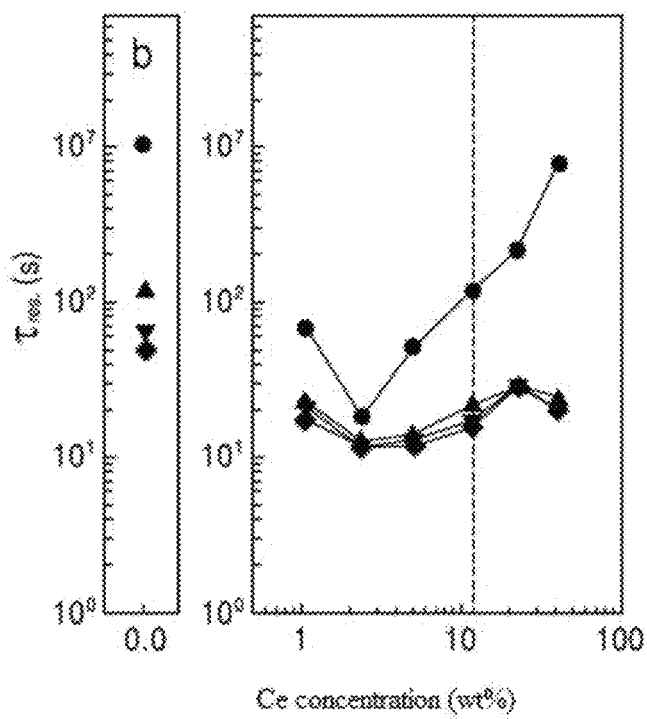
[Fig. 23a]
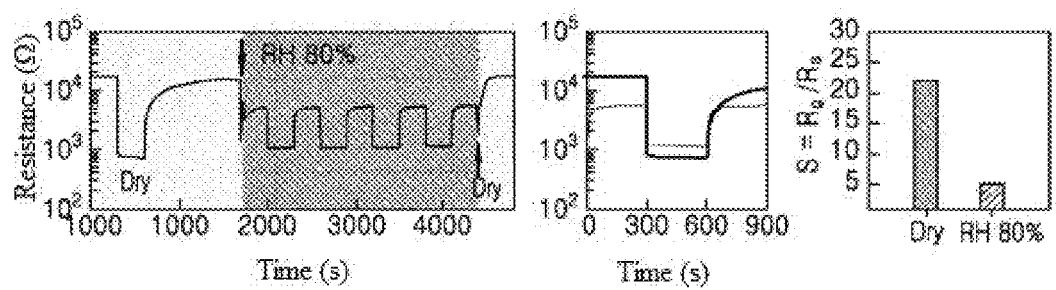
[Fig. 23b]
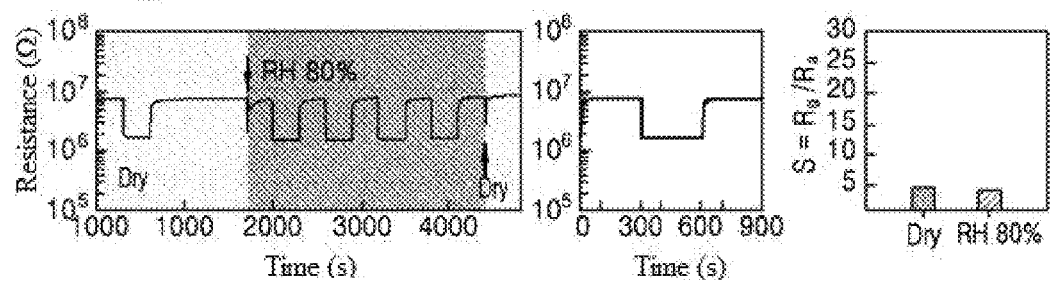

[Fig. 24a]
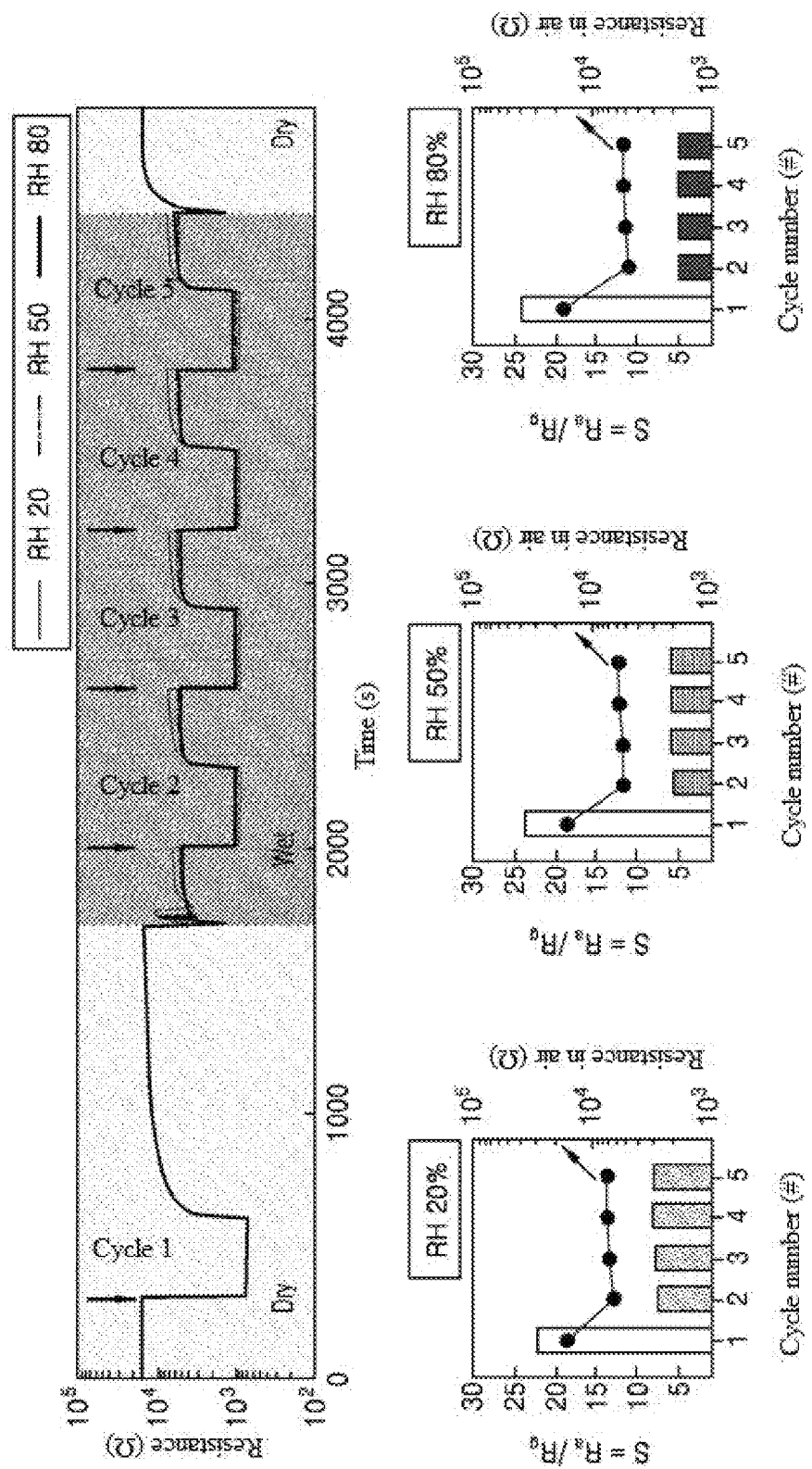

[Fig. 24b]
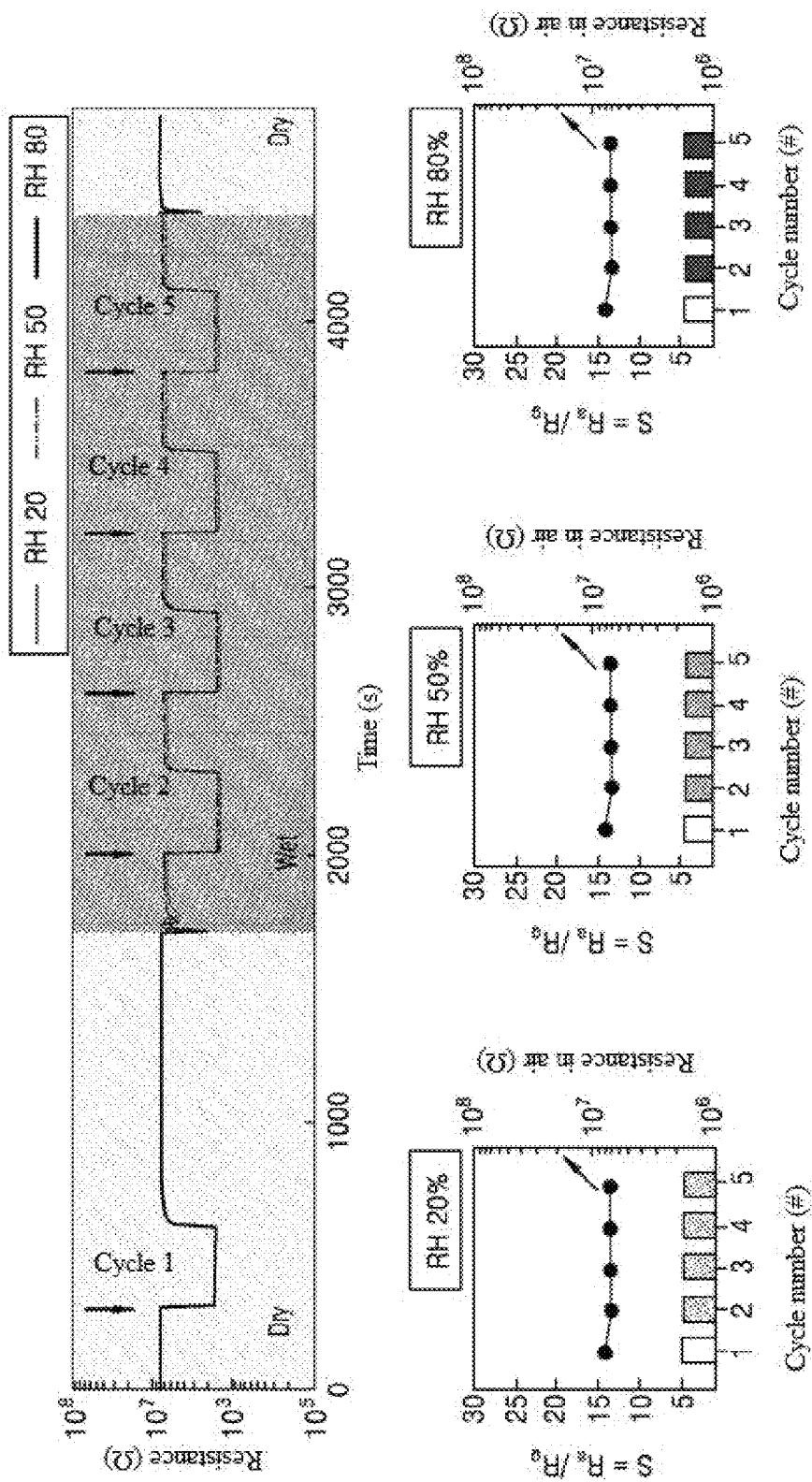

[Fig. 25a]
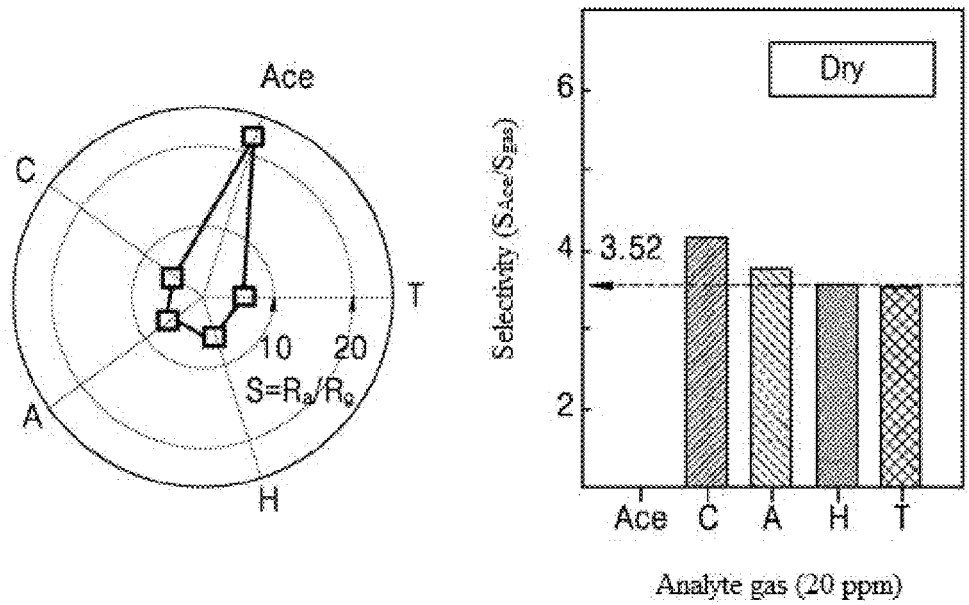
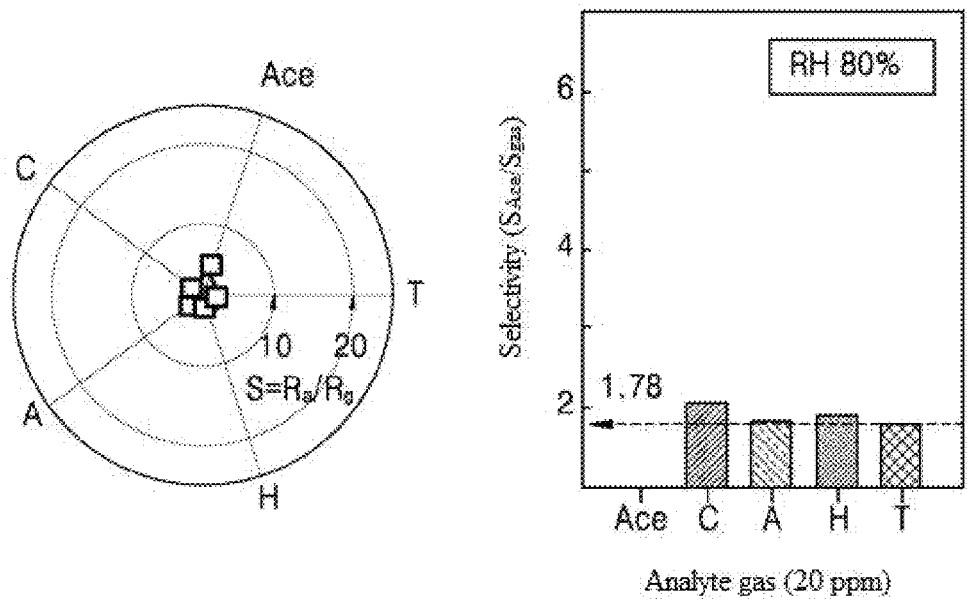

[Fig. 25b]
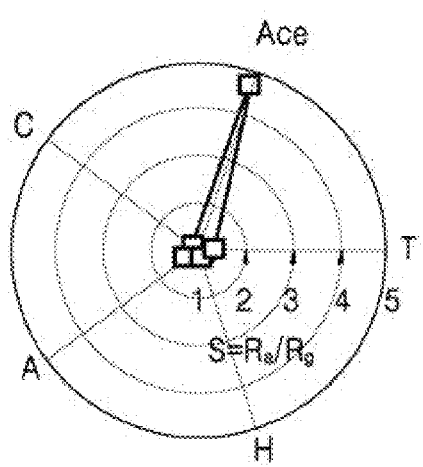
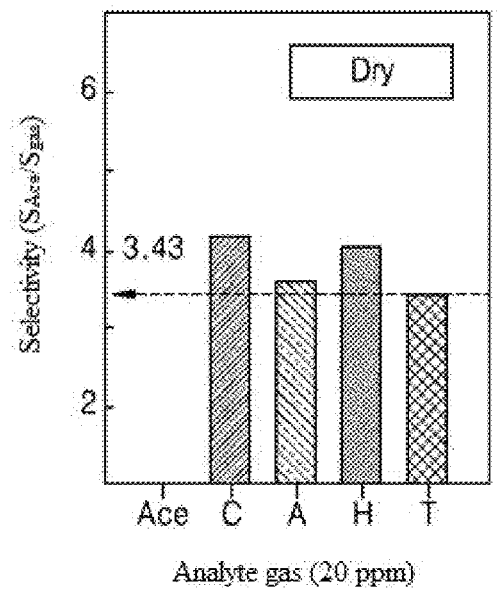
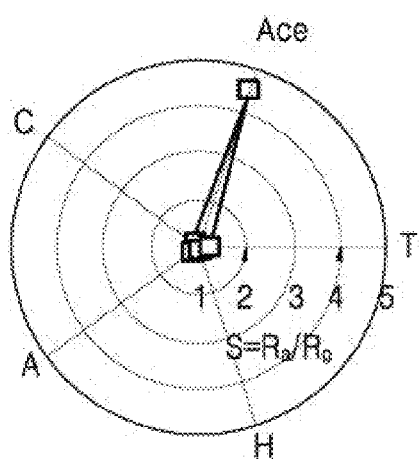
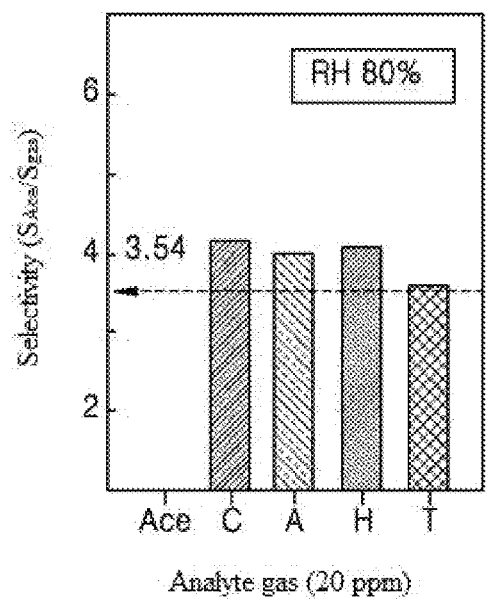

[Fig. 26a]
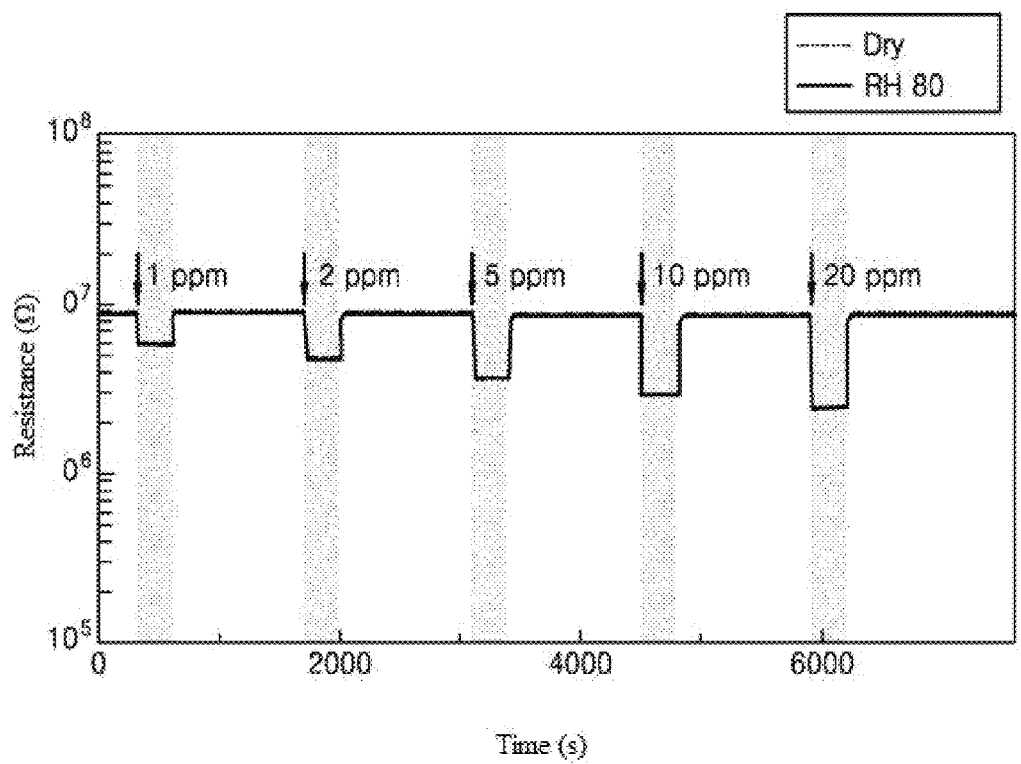

[Fig. 26b]
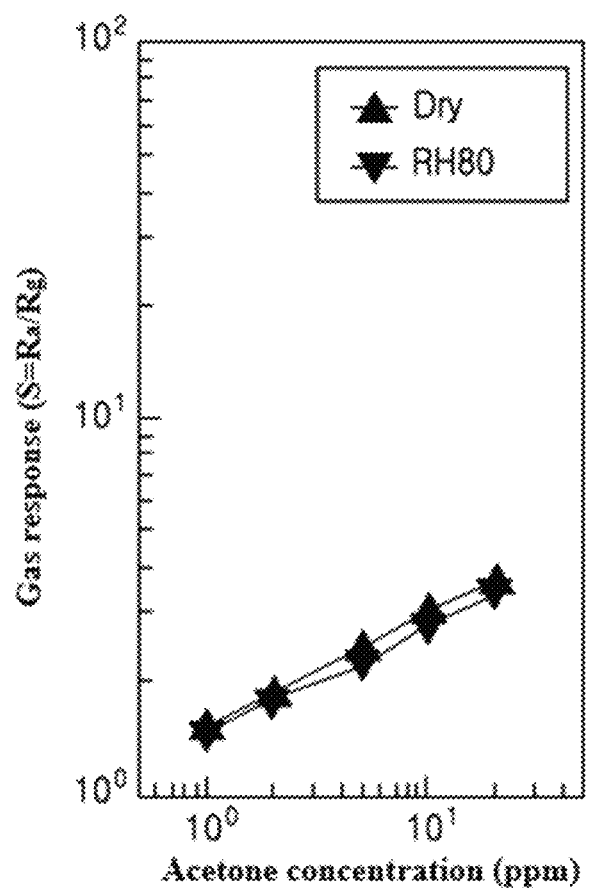
[Fig. 27]
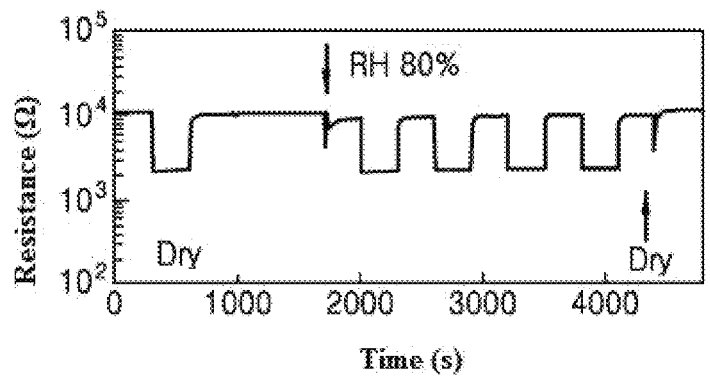

GAS DETECTION COMPOSITE COMPRISING CEO2 UNIFORMLY LOADED ON OXIDE NANOSTRUCTURE AND METHOD OF PREPARATION THEREOF

TECHNICAL FIELD

The present invention relates to a composite having the ability to stably and reliably detect a target gas even in a moist environment, methods for preparing the composite, a gas sensor including the composite as a material for a gas sensing layer, and a method for fabricating the gas sensor.

BACKGROUND ART

Since the first proposal by Professor Seiyama, et al. at Kyushu University in the 1960's, oxide semiconductor gas sensors have been widely used in various applications, including measurement of drivers' blood alcohol levels, detection of explosive gases, detection of exhaust gases, and detection of harmful gases, due to their advantages of high sensitivity, miniaturization, integration, simple operating circuits, and economical prices. With the recent growing interest in human health and environmental pollution, there has been a rapidly increasing demand for gas sensors for the detection of indoor/outdoor environmental gases, gas sensors for self-diagnosis of diseases, and artificial olfactory sensors mountable on mobile devices. However, oxide semiconductor gas sensors tend to respond to external moisture, deteriorating their performance and reliability. These fundamental problems are still obstacles to the commercialization of oxide semiconductor gas sensors.

Oxide semiconductor gas sensors detect target gases based on resistance variation caused when reducing gases react with oxygen ions adsorbed on the oxide surface. Moisture in air behaves like an analyte gas that first consumes oxygen ions on the oxide surface of oxide semiconductor gas sensors, resulting in a remarkable reduction in gas response and a change in sensor resistance. Further, oxide semiconductor gas sensors operating in air are inevitably exposed to moisture. Since humidity varies greatly depending on various factors such as weather, season, and day/night alternation, it is almost impossible to ensure stable gas sensing characteristics of gas sensors without removing their humidity dependence. Particularly, moisture is generally present at a concentration of about several thousands to about several tens of thousands of ppm in air, which is much higher than the typical concentrations (several to several tens of ppm) of analyte gases. For this reason, humidity-dependent changes in resistance and gas response should be considered the most important factors in ensuring the reliability of sensors. Remarkable performance and reliability deterioration of oxide semiconductor gas sensors in the presence of moisture is still a problem that has been difficult to solve for about five decades since the first proposal of gas sensors and is a major impediment to the commercialization of gas sensors. That is, constant gas response and resistance irrespective of the presence and concentration of moisture are prerequisites for the development of highly reliable gas sensors that can be utilized in various applications.

Specifically, since moisture in air reacts just like analyte gases on the surface of oxide semiconductors, oxide semiconductor gas sensors encounter the following serious problems: (1) considerable changes in resistance and gas response caused by moisture and (2) reduced gas response to one-severalth to one-several tenths in a highly moist atmosphere. Under these circumstances, moisture stability of sensor materials is currently emerging as the most important issue in the field of oxide semiconductor gas sensors. However, most (≥99%) of the studies on oxide semiconductor gas sensors have still focused on the evaluation of gas sensing characteristics in a dry atmosphere and little research has been done on gas sensors in a moist atmosphere. Only 12 studies have been conducted on changes in gas sensing characteristics caused by moisture for the past 4 years. Most of studies, except for the study reported by Kim et al. (Non-patent Document 1), did not propose effective approaches to improve the characteristics of sensors and simply mention problems encountered in the studies.

Also in the study by Kim et al., Ni ions penetrate $SnO_2$ lattice to form acceptor levels, causing a remarkable increase in the resistance of the sensor and a reduction in the gas response of the sensor. These problems make it impossible to ensure selectivity of the sensor for a particular gas. Another problem of the sensor is that a very long time is required until the resistance of the sensor in a moist atmosphere reaches a level similar to that in a dry atmosphere. The reason why little research has been conducted on such important issues is because of the fundamental problem that sensing materials with higher gas reactivity are more highly reactive with moisture. Therefore, designing additives capable of reducing or eliminating the humidity dependence of gas sensors rather than finding new highly sensitive materials would be effective in solving the problem of humidity dependence.

In this connection, the present inventors were aware of the above-described problems and reported composites for gas detection including an indium oxide hollow structure and cerium oxide nanoparticles and methods for preparing the composites to provide gas sensors that can exhibit ultrahigh sensitivity, high selectivity, and rapid response to various reducing gases without the influence of moisture (Patent Document 1).

Patent Document 1: Korean Patent Publication No. 10-1594734

Non-Patent Document 1: H.-R. Kim, Adv. Funct. Mater. 21 (2011) 4456-4463

DETAILED DESCRIPTION OF THE INVENTION

Problems to be Solved by the Invention

Thus, the present invention intends to provide a composite for highly reliable gas detection in which $CeO_2$ as an additive is uniformly loaded on an oxide semiconductor nanostructure and methods for preparing the composite. The present invention also intends to provide a gas sensor including the composite as a material for a gas sensing layer that can detect a target gas with high gas response irrespective of the presence and concentration of moisture and whose resistance can reach a constant level in a very short time, and a method for fabricating the gas sensor.

Means for Solving the Problems

One aspect of the present invention provides a composite for gas detection including: a nanostructure of an oxide semiconductor selected from the group consisting of $SnO_2$, $ZnO$, $WO_3$, $NiO$, and $In_2O_3$; and a $CeO_2$ additive loaded on the nanostructure.

According to one embodiment of the present invention, the nanostructure may have a hollow or yolk-shell structure.

According to a further embodiment of the present invention, the $CeO_2$ additive may be coated on the surface of the nanostructure.

According to another embodiment of the present invention, the $CeO_2$ additive may be loaded in an amount of 3% to 30% by weight, based on the total weight of the composite.

According to another embodiment of the present invention, the gas may be a reducing gas selected from the group consisting of acetone, formaldehyde, ethanol, carbon monoxide, xylene, toluene, benzene, and mixtures thereof.

A further aspect of the present invention provides a method for preparing a composite for gas detection, including: a) preparing a solution including at least one salt selected from the group consisting of Sn, Zn, W, Ni, and In salts, a Ce salt, and an organic acid or sugar; b) subjecting the solution to spray pyrolysis through spray pyrolysis equipment; and c) collecting the spray pyrolysis product in the form of a fine powder.

According to one embodiment of the present invention, the Sn salt may be selected from the group consisting of $SnC_2O_4$, $SnCl_4 \cdot xH_2O$ (x is 2 or 5), $Sn(CH_3COO)_4$, and mixtures thereof; the Zn salt may be selected from the group consisting of $Zn(NO_3)_2 \cdot 6H_2O$, $ZnCl_2$, $Zn(CH_3COO)_2 \cdot 2H_2O$, and mixtures thereof; the W salt may be selected from the group consisting of $WO_3$, $(NH_4)_{10}H_2(W_2O_7)_6$, and mixtures thereof; the Ni salt may be selected from the group consisting of $Ni(NO_3)_2 \cdot 6H_2O$, $NiCl_2 \cdot 6H_2O$, $Ni(CH_3COO)_2 \cdot 4H_2O$, and mixtures thereof the In salt may be selected from the group consisting of $In(NO_3)_3 \cdot xH_2O$ (x=2, 6 or 9) and mixtures thereof the Ce salt may be selected from the group consisting of $Ce(NO_3)_3 \cdot 6H_2O$, $Ce(SO_4)_2 \cdot 4H_2O$, $CeCl_3 \cdot 4H_2O$, and mixtures thereof; the organic acid may be selected from the group consisting of citric acid, ethylene glycol, and mixtures thereof and the sugar may be selected from the group consisting of sucrose, glucose, and mixtures thereof.

According to a further embodiment of the present invention, in step b), the spray pyrolysis may be performed by spraying the solution into an electric furnace heated to 600° C. to 1100° C. at a rate of 2 L/m to 50 L/m.

Another aspect of the present invention provides a method for preparing a composite for gas detection, including: a) preparing a dispersion of at least one salt selected from the group consisting of Sn, Zn, W, Ni, and In salts in a solvent; b) adding a Ce salt to the dispersion and reducing the mixture solution; and c) collecting the reduction product in the form of a fine powder.

According to one embodiment of the present invention, the Sn salt may be selected from the group consisting of $SnC_2O_4$, $SnCl_4 \cdot xH_2O$ (x is 2 or 5), $Sn(CH_3COO)_4$, and mixtures thereof; the Zn salt may be selected from the group consisting of $Zn(NO_3)_2 \cdot 6H_2O$, $ZnCl_2$, $Zn(CH_3COO)_2 \cdot 2H_2O$, and mixtures thereof; the W salt may be selected from the group consisting of $WO_3$, $(NH_4)_{10}H_2(W_2O_7)_6$, and mixtures thereof; the Ni salt may be selected from the group consisting of $Ni(NO_3)_2 \cdot 6H_2O$, $NiCl_2 \cdot 6H_2O$, $Ni(CH_3COO)_2 \cdot 4H_2O$, and mixtures thereof; the In salt may be selected from the group consisting of $In(NO_3)_3 \cdot xH_2O$ (x=2, 6 or 9) and mixtures thereof; and the Ce salt may be selected from the group consisting of $Ce(NO_3)_3 \cdot 6H_2O$, $Ce(SO_4)_2 \cdot 4H_2O$, $CeCl_3 \cdot 4H_2O$, and mixtures thereof.

According to a further embodiment of the present invention, in step b), the mixture solution may be reduced by adding a reducing agent selected from the group consisting of sodium borohydride ($NaBH_4$), hydrazine, and mixtures thereof.

Another aspect of the present invention provides a gas sensor for gas detection including the composite as a material for a gas sensing layer.

Yet another aspect of the present invention provides a method for fabricating a gas sensor including: preparing a solution including the composite and a binder; and coating the solution on a substrate, followed by drying and annealing.

According to one embodiment of the present invention, the coating may be performed by a drop coating process, the drying may be performed at 70° C. to 120° C. for 12 hours to 24 hours, and the annealing may be performed at 500° C. to 900° C. for 1 hour to 6 hours.

Effects of the Invention

The composite for gas detection according to the present invention uses an oxide semiconductor nanostructure uniformly loaded with $CeO_2$. The composite can rapidly detect an analyte gas with high gas response irrespective of the presence and concentration of moisture. The sensor of the present invention includes the composite as a material for a gas sensing layer.

BRIEF DESCRIPTION OF THE DRAWINGS

FIG. 1 is a flow chart schematically illustrating a method for fabricating gas sensors including composites having hollow structures prepared based on ultrasonic spray pyrolysis in Examples 1-1 and 1-2.

FIG. 2 is a flow chart schematically illustrating a method for fabricating gas sensors including composites having yolk-shell structures prepared based on ultrasonic spray pyrolysis in Examples 2-1 and 2-2.

FIG. 3 is a flow chart schematically illustrating a method for fabricating a gas sensor including a composite prepared based on solution stirring in Example 3.

FIGS. 4a, 4b, 4c, 4d, 4e, 4f, 4g and 4h show SEM images of fine powders synthesized based on ultrasonic spray pyrolysis in Comparative Example 1-1 (hollow pristine $SnO_2$, a), Comparative Example 1-2 (hollow pristine ZnO, c), Comparative Example 2-1 (yolk-shell $WO_3$, e), Comparative Example 2-2 (yolk-shell NiO, g), Example 1-1 (b), Example 1-2 (d), Example 2-1 (f), and Example 2-2 (h).

FIGS. 5a and 5b show SEM images of a fine powder synthesized based on solution stirring in Example 3 (b) and a commercial $SnO_2$ fine powder (Comparative Example 3, a).

FIG. 6 shows the results of XRD phase analysis for fine powders prepared in Example 1-1 (a2), Comparative Example 1-1 (a1), Example 1-2 (b2), Comparative Example 1-2 (b1), Example 2-1 (c2), Comparative Example 2-1 (c1), Example 2-2 (d2), and Comparative Example 2-2 (d1).

FIG. 7 shows the results of XRD phase analysis for fine powders prepared in Example 3 (a2) and Comparative Example 3 (a1).

FIGS. 8a1, 8a2, 8b1 and 8b2 compare the gas sensing transients of gas sensors fabricated in Comparative Example 1-1 (a1,a2) and Example 1-1 (b1,b2) to 20 ppm acetone in a dry atmosphere and at a relative humidity of 80%, which were measured at 450° C.

FIGS. 9a, 9b, 9c, 9d, 9e, 9f, 9g and 9h compare the gas responses of gas sensors fabricated in Comparative Example 1-1 (a), Example 1-1 (b), Comparative Example 1-2 (c), Example 1-2 (d), Comparative Example 2-1 (e), Example 2-1 (f), Comparative Example 2-2 (g), and Example 2-2 (h)

to 20 ppm acetone in a dry atmosphere and at relative humidities 20, 50, and 80%, which were measured at 450° C.

FIGS. 10a, 10b, 10c, 10d, 10e, 10f, 10g and 10h compare the resistances of gas sensors fabricated in Comparative Example 1-1 (a), Example 1-1 (b), Comparative Example 1-2 (c), Example 1-2 (d), Comparative Example 2-1 (e), Example 2-1 (f), Comparative Example 2-2 (g), and Example 2-2 (h) in a dry atmosphere and at relative humidities of 20, 50, and 80%, which were measured at 450° C.

FIGS. 11a, 11b, 11c and 11d compare the acetone (20 ppm) gas responses and resistances of gas sensors fabricated in Comparative Example 3 (a,c) and Example 3 (b,d) in a dry atmosphere and at relative humidities of 20, 50, and 80%, which were measured at 450° C.

FIG. 12 is a flow chart schematically illustrating a method for preparing a composite for gas detection based on a layer-by-layer process according to one embodiment of the present invention.

FIG. 13 is a flow chart schematically illustrating a method for preparing a composite for gas detection based on a batch process according to a further embodiment of the present invention.

FIGS. 14a, 14b, 14c, 14d, 14e, 14f, 14g, 14h and 14i are SEM images of a fine powder of pristine $In_2O_3$ having a hollow structure (Comparative Example 4) and fine powders in which 1.04 wt % (Comparative Example 5-1), 2.33 wt % (Comparative Example 5-2), 4.97 wt % (Example 4-2), 11.7 wt % (Example 4-1), 22.4 wt % (Example 4-3), 39.9 wt % (Example 4-4), 45.6 wt % (Comparative Example 5-3), and 55.0 wt % (Comparative Example 5-4) of $CeO_2$ nanoparticles were uniformly coated on the surfaces of $In_2O_3$ hollow structures, respectively.

FIGS. 15a, 15b, 15c, 15d, 15e, 15f and 15g are TEM images of fine powders prepared in Comparative Example 4 (FIGS. 15a to 15c) and Example 4-1 (FIGS. 15d to 15g).

FIGS. 16a, 16b, 16c, 16d, 16e, 16f, 16g and 16h are TEM images of fine powders prepared in Example 4-3 (FIGS. 16a to 16d) and Example 4-4 (FIGS. 16e to 16h).

FIGS. 17a, 17b, 17c and 17d are SEM and TEM images of a fine powder prepared in Example 5.

FIG. 18 shows the results of X-ray phase analysis for fine powders prepared in Comparative Example 4 (a-1, a-2, and a-3), Comparative Example 5-1 (b-1, b-2, and b-3), Comparative Example 5-2 (c-1, c-2, and c-3), Example 4-2 (d-1, d-2, and d-3), Example 4-1 (e-1, e-2, and e-3), Example 4-3 (f-1, f-2, and f-3), Example 4-4 (g-1, g-2, and g-3), Comparative Example 5-3 (h-1, h-2, and h-3), and Comparative Example 5-4 (i-1, i-2, and i-3).

FIG. 19 shows the results of XPS analysis for fine powders prepared in Comparative Example 4 (a-1, a-2, a-3, and a-4), Comparative Example 5-1 (b-1, b-2, b-3, and b-4), Comparative Example 5-2 (c-1, c-2, c-3, and c-4), Example 4-2 (d-1, d-2, d-3, and d-4), Example 4-1 (e-1, e-2, e-3, and e-4), Example 4-3 (f-1, f-2, f-3, and f-4), Example 4-4 (g-1, g-2, g-3, and g-4), Comparative Example 5-3 (h-1, h-2, h-3, and h-4), and Comparative Example 5-4 (i-1, i-2, i-3, and i-4).

FIGS. 20a and 20b show changes in the resistance and gas response of sensors fabricated in Example 4-1 (FIG. 20a) and Comparative Example 4 (FIG. 20b) to 20 ppm acetone, 20 ppm ethanol, 200 ppm hydrogen, 200 ppm carbon monoxide, 200 ppm hydrogen, 100 ppm toluene, 200 ppm ammonia, and 50 ppm formaldehyde in a dry atmosphere and at a relative humidity of 80%, which were measured at a sensing temperature of 450° C.

FIGS. 21a, 21b, 21c and 21d show the gas responses of fine powders prepared in Comparative Example 4, Comparative Example 5-1, Comparative Example 5-2, Example 4-2, Example 4-1, Example 4-3, and Example 4-4 to 20 ppm acetone in a dry atmosphere and at relative humidities of 20%, 50%, and 80%, which were measured at a sensing temperature of 450° C. (FIG. 21a), and resistances (FIG. 21b), humidity-dependent gas response variations (FIG. 21c) and resistance variations (21d) of the fine powders.

FIGS. 22a and 22b show 90% gas response times (FIG. 22a) and 90% recovery times (FIG. 22b) of fine powders prepared in Comparative Example 4, Comparative Example 5-1, Comparative Example 5-2, Example 4-2, Example 4-1, Example 4-3 and Example 4-4 in a dry atmosphere and at relative humidities 20%, 50%, and 80% for 20 ppm acetone.

FIGS. 23a and 23b show the gas sensing transients and gas responses of fine powders prepared in Comparative Example 4 (FIG. 23a) and Example 4-1 (FIG. 23b) in a dry atmosphere and at a relative humidity of 80% to 20 ppm acetone.

FIGS. 24a and 24b show the gas sensing transients of fine powders prepared in Comparative Example 4 (FIG. 24a) and Example 4-1 (FIG. 24b) to 20 ppm acetone in a dry atmosphere and at relative humidities of 20%, 50%, and 80% and changes in the resistance and gas response of the fine powders in a dry atmosphere and at relative humidities of 20%, 50%, and 80% as a function of the number of measurements.

FIGS. 25a and 25b show the gas responses and selectivities of fine powders prepared in Comparative Example 4 (FIG. 25a) and Example 4-1 (FIG. 25b) in a dry atmosphere and at a relative humidity of 80%.

FIGS. 26a and 26b show the transients and gas responses of a fine powder prepared in Example 4-1 to different concentrations of acetone gas in a dry atmosphere and at a relative humidity of 80%.

FIG. 27 shows the gas sensing transients of a fine powder prepared in Example 5 to 20 ppm acetone.

BEST MODE FOR CARRYING OUT THE INVENTION

The present invention will now be described in more detail.

In an effort to solve the problems of the prior art, the present invention provides a composite for gas detection based on an oxide semiconductor nanostructure uniformly loaded with $CeO_2$. The oxide semiconductor nanostructure acts as a major gas sensing material for the detection of an analyte gas and the loaded $CeO_2$ acts to selectively absorb and remove moisture entering from the outside.

$CeO_2$ is an ionic conductor to very rapidly transition between lattice oxygen and oxygen ions due to its good ability to switch valence states. It was reported that $CeO_2$ can serve to remove hydroxyl groups formed on the surface of PEM after long-term operation in the field of PEMFC (V. Prabhakaran, PNAS (2012) 109, 1029-1034). Thus, the present inventors have thought that coating of $CeO_2$ nanoparticles on the surface of a gas sensing material can induce the reverse reaction of the water adsorption reaction depicted in Reaction 1:

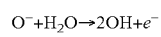
$$O^- + H_2O \rightarrow 2OH + e^-$$  <Reaction 1>

As a result of actual measurement, the humidity dependence of the sensor was reduced to a negligible level. The CeO$_2$ nanoparticles are determined to remove the humidity dependence of the sensor according to the following reactions:

$$4Ce^{4+}+2H_2O \rightarrow 4Ce^{3+}+4H^++O_2 \quad \text{<Reaction 2>}$$

$$O_{(M)}^-+H_2O \rightarrow 2OH_{(M)}+e_{(M)}^- \quad \text{<Reaction 3>}$$

$$OH_{(M)}+Ce^{3+}+H^+ \rightarrow Ce^{4+}+H_2O \quad \text{<Reaction 4>}$$

$$\tfrac{1}{2}O_2+e_{(M)}^- \rightarrow O_{(M)}^- \quad \text{<Reaction 5>}$$

That is, Ce$^{4+}$ in the CeO$_2$ nanoparticles reacts with water, with the result that it is converted to Ce$^{3+}$ and H$^+$ and oxygen are generated (Reaction 2). The Ce$^{3+}$ and H$^+$ react with hydroxyl groups formed on the surface of the gas sensing material as a result of Reaction 3. The Ce$^{3+}$ is oxidized to Ce$^{4+}$ and water is produced, as depicted in Reaction 4. Then, the water is desorbed. Finally, the oxygen generated in Reaction 2 reacts with the electron injected on the surface of the gas sensing material (Reaction 3) to regenerate an oxygen ion (Reaction 5).

This series of reactions is repeated to prevent the surface of the sensor from being poisoned by moisture due to the good ability of CeO$_2$ to switch valence states (L. Xu, Inorg. Chem. 49 (2010) 10590-10597).

Based on the series of reactions, the CeO$_2$ nanoparticles protect the oxide semiconductor nanostructure, such as SnO$_2$, ZnO, WO$_3$, NiO or In$_2$O$_3$, as a main sensing material against a large quantity of moisture continuously supplied from the outside to minimize or eliminate the humidity dependence of the sensor. The reactions take place only at the interfaces adjacent to areas where CeO$_2$ is in contact with the gas sensing material. For this reason, it is necessary to coat above a predetermined amount of the CeO$_2$ nanoparticles on the surface of the gas sensing material in order to protect a large portion of the surface of the gas sensing material against moisture. However, when an excess of the CeO$_2$ is coated, the CeO$_2$ nanoparticles may be connected to one another, causing a change in the resistance of the sensor or impeding conduction through the gas sensing material. Therefore, CeO$_2$ needs to be discretely and uniformly distributed at an optimal concentration over the entire surface of the gas sensing material for effective removal of moisture supplied from the outside with minimal influence of CeO$_2$ on the resistance variation and gas sensing response of the sensor.

Thus, the present invention provides a composite for gas detection including: a nanostructure of an oxide semiconductor selected from the group consisting of SnO$_2$, ZnO, WO$_3$, NiO, and In$_2$O$_3$; and a CeO$_2$ additive loaded on the nanostructure.

The nanostructure may have a hollow or yolk-shell structure, as described below. When the oxide semiconductor is SnO$_2$, ZnO or In$_2$O$_3$, the nanostructure may have a hollow structure. Alternatively, when the oxide semiconductor is WO$_3$ or NiO, the nanostructure may have a yolk-shell structure.

The CeO$_2$ additive may be coated on the surface of the nanostructure in order to effectively protect the nanostructure against moisture and minimize the influence of moisture on gas sensing response of the nanostructure.

Furthermore, the CeO$_2$ additive may be loaded in an amount of 3% to 30% by weight, based on the total weight of the composite. If the CeO$_2$ additive is loaded in an amount of less than 3% by weight, its effect on protecting the gas sensing material against moisture is insignificant. Meanwhile, if the CeO$_2$ additive is loaded in an amount exceeding 30%, the CeO$_2$ nanoparticles are connected to one another, causing a change in resistance or impeding conduction through the gas sensing material.

The composite of the present invention can be used to detect a reducing gas selected from the group consisting of gaseous volatile organic compounds, including acetone, formaldehyde, ethanol, carbon monoxide, xylene, toluene, benzene, and mixtures thereof.

The present invention also provides a method for preparing the composite for gas detection, including: a) preparing a solution including at least one salt selected from the group consisting of Sn, Zn, W, Ni, and In salts, a Ce salt, and an organic acid or sugar; b) subjecting the solution to spray pyrolysis through spray pyrolysis equipment; and c) collecting the spray pyrolysis product in the form of a fine powder.

The Sn salt is selected from the group consisting of, but not limited to, SnC$_2$O$_4$, SnCl$_4$.xH$_2$O (x is 2 or 5), Sn(CH$_3$COO)$_4$, and mixtures thereof; the Zn salt is selected from the group consisting of, but not limited to, Zn(NO$_3$)$_2$.6H$_2$O, ZnCl$_2$, Zn(CH$_3$COO)$_2$.2H$_2$O, and mixtures thereof; the W salt is selected from the group consisting of, but not limited to, WO$_3$, (NH$_4$)$_{10}$H$_2$(W$_2$O$_7$)$_6$, and mixtures thereof; the Ni salt is selected from the group consisting of, but not limited to, Ni(NO$_3$)$_2$.6H$_2$O, NiCl$_2$.6H$_2$O, Ni(CH$_3$COO)$_2$.4H$_2$O, and mixtures thereof; the In salt is selected from the group consisting of, but not limited to, In(NO$_3$)$_3$.xH$_2$O (x=2, 6 or 9) and mixtures thereof; and the Ce salt is selected from the group consisting of, but not limited to, Ce(NO$_3$)$_3$.6H$_2$O, Ce(SO$_4$)$_2$.4H$_2$O, CeCl$_3$.4H$_2$O, and mixtures thereof.

CeO$_2$ may be added to the hollow nanostructure formed using the Sn, Zn or In salt. In this case, an organic acid or sugar is added to the solution prepared in step a). The organic acid may be selected from the group consisting of citric acid, ethylene glycol, and mixtures thereof.

Alternatively, CeO$_2$ may be added to the yolk-shell nanostructure formed using the W or Ni salt. In this case, a sugar selected from the group consisting of sucrose, glucose, and mixtures thereof may be added to the solution prepared in step a).

The spray pyrolysis may be performed by spraying the solution prepared in step a) into an electric furnace heated to 600° C. to 1100° C. at a rate of 2 L/m to 50 L/m.

The composite of the present invention may also be prepared based on solution stirring instead of based on spray pyrolysis. In this case, the composite of the present invention may be prepared by a method including: a) preparing a dispersion of at least one salt selected from the group consisting of Sn, Zn, W, Ni, and In salts in a solvent; b) adding a Ce salt to the dispersion and reducing the mixture solution; and c) collecting the reduction product in the form of a fine powder.

The Sn, Zn, W, Ni, In, and Ce salts are the same as those described in the method based on spray pyrolysis.

In the method based on solution stirring, the mixture solution should be reduced by a reducing agent for the preparation of the CeO$_2$-loaded nanostructure. The reducing agent may be selected from the group consisting of NaBH$_4$, hydrazine, and mixtures thereof.

Alternatively, the composite of the present invention may be prepared based on a layer-by-layer process. In this case, the composite of the present invention may be prepared by a method including: preparing a solution including an In salt and a sugar; subjecting the solution to spray pyrolysis through spray pyrolysis equipment; adding surface charge modifiers to the spray pyrolysis product to obtain a powder in which charges are introduced on the surface of the spray pyrolysis product; mixing a dispersion of the powder with a Ce salt solution; and adding a reducing agent to the mixture solution, followed by washing and drying to obtain a fine powder.

The kinds of the In salt, Ce salt, and the sugar, the weight ratio of the Ce salt to the In salt, and the spray pyrolysis conditions are the same as those described in the method based on spray pyrolysis.

Referring to FIG. 12, the method based on a layer-by-layer process is different from the method based on spray pyrolysis in that a solution including an In salt and a sugar is prepared (S1), the solution is subjected to spray pyrolysis to prepare an $In_2O_3$ hollow structure as a main sensing material (S2), and the spray pyrolysis product is mixed with a solution of surface charge modifiers to introduce charges on the surface of the main sensing material (S3).

In S3, charges may be introduced by sequentially adding a surface positive charge modifier and a surface negative charge modifier. The surface positive charge modifier may be selected from the group consisting of polyethyleneimine, poly(allylamine hydrochloride), poly(diallyldimethylammonium chloride), and mixtures thereof. The surface negative charge modifier may be selected from the group consisting of polyacrylic acid, poly(styrenesulfonate), poly(vinylsulfonate), and mixtures thereof.

After charges are introduced using the surface charge modifiers, the resulting powder is mixed with a Ce salt solution in order to disperse $CeO_2$ nanoparticles on the surface of the main sensing material (S4). This procedure allows Ce ions to form electrostatic bonds with the negative (−) charges on the $In_2O_3$ surface. Thereafter, a reducing agent is added to reduce the Ce ions to $CeO_2$ nanoparticles (S5). After the reduction, the $CeO_2$ nanoparticles are washed and dried to prepare the desired composite for gas detection in the form of a dry fine powder (S6). The reducing agent may be selected from the group consisting of sodium borohydride, hydrazine, and mixture thereof.

The present invention also provides a gas sensor for gas detection including the composite as a material for a gas sensing layer. The gas sensor may be fabricated by a method including: preparing a solution including the composite and a binder; and coating the solution on a substrate, followed by drying and annealing. The coating may be performed by a drop coating process, the drying may be performed at 70° C. to 120° C. for 12 hours to 24 hours, and the annealing may be performed at 500° C. to 900° C. for 1 hour to 6 hours.

MODE FOR CARRYING OUT THE INVENTION

The present invention will be explained in more detail with reference to the following examples. These examples are provided to assist in understanding the invention and are not intended to limit the scope of the invention.

Acetone is an indoor/outdoor environmental pollution gas and is a biomarker gas that is detected in the exhaled breath of patients with diabetes. Accordingly, selective detection of acetone irrespective of the presence and concentration of moisture is of great importance. In view of this, acetone was selected as a main analyte gas and the influences of external moisture on the sensing characteristics (e.g., gas response and resistance) of sensors were analyzed in the following examples.

Gas sensors were fabricated using a fine powder of pristine $SnO_2$ having a hollow structure (Comparative Example 1-1), a fine powder of pristine ZnO having a hollow structure (Comparative Example 1-2), a fine powder of pristine $WO_3$ having a yolk-shell structure (Comparative Example 2-1), and a fine powder of pristine NiO having a yolk-shell structure (Comparative Example 2-2). Gas sensors were fabricated using a $SnO_2$ hollow structure loaded with 3 wt % $CeO_2$ (Example 1-1), a ZnO hollow structure loaded with 5 wt % $CeO_2$ (Example 1-2), a $WO_3$ yolk-shell structure loaded with 12 wt % $CeO_2$ (Example 2-1), and a NiO yolk-shell structure loaded with 30 wt % $CeO_2$ (Example 2-2), which were prepared based on ultrasonic spray pyrolysis. The humidity dependencies, gas responses, and resistances of the gas sensors were compared. A gas sensor was fabricated using a fine powder of a $SnO_2$ hollow structure loaded with 3 wt % $CeO_2$ nanoparticles prepared based on solution stirring (Example 3). Differences in the humidity dependencies and gas sensing characteristics of the gas sensors including the composites prepared based on different synthesis methods were evaluated. FIG. 1 is a flow chart schematically illustrating a method for fabricating the gas sensors including the composites having hollow structures prepared based on ultrasonic spray pyrolysis in Examples 1-1 and 1-2, FIG. 2 is a flow chart schematically illustrating a method for fabricating the gas sensors including the composites having yolk-shell structures prepared based on ultrasonic spray pyrolysis in Examples 2-1 and 2-2, and FIG. 3 is a flow chart schematically illustrating a method for fabricating the gas sensor including the composite prepared based on solution stirring in Example 3.

A gas sensor was fabricated using a fine powder of pristine $In_2O_3$ having a hollow structure (Comparative Example 4), and gas sensors were fabricated in which 1.04 wt % (Comparative Example 5-1), 2.33 wt % (Comparative Example 5-2), 4.97 wt % (Example 4-2), 11.7 wt % (Example 4-1), 22.4 wt % (Example 4-3), 39.9 wt % (Example 4-4), 45.6 wt % (Comparative Example 5-3), and 55.0 wt % (Comparative Example 5-4) of $CeO_2$ nanoparticles were uniformly coated on the surfaces of $In_2O_3$ hollow structures and their humidity dependencies, gas responses, resistances, response/recovery rates, and selectivities for acetone were compared. A gas sensor of Example 5 was fabricated in the same manner as in Example 4, except that the surface of the fine powder was not modified. In the gas sensor of Example 5, 5.7 wt % $CeO_2$ nanoparticles were uniformly coated on the surface of the $In_2O_3$ hollow structure.

Example 1-1 and Comparative Example 1-1

0.05 M tin oxalate ($SnC_2O_4$, 98%, Sigma-Aldrich, USA) and 0.15 M citric acid monohydrate ($C_6H_8O_7.H_2O$, ≥99.0%, Sigma-Aldrich, USA) were stirred in 300 mL of triple-distilled water for 30 min to prepare a spray solution. To the spray solution was added Ce nitrate hexahydrate ($Ce(NO_3)_3.6H_2O$, 99.99%, Sigma-Aldrich, USA) in such an amount that the weight ratio of Ce to Sn was 3:97. After stirring for 5 min, the mixture was ultrasonically sprayed to form microdroplets. The microdroplets were instantaneously annealed while passing through a reaction furnace ($O_2$) at 900° C. at a flow rate of 5 L·min$^{-1}$, giving a $SnO_2$ hollow structure uniformly loaded with 3 wt % $CeO_2$ (Example 1-1). $CeO_2$-unloaded pristine $SnO_2$ having a hollow structure was synthesized in the same manner as described above, except that no Ce source was added (Comparative Example 1-1).

Each of the fine powders thus synthesized was mixed with triple-distilled water, drop coated on an alumina substrate where an Au electrode was disposed, and annealed at 500° C. for 2 h to fabricate a gas sensor. Changes in the resistance of the sensor were measured at 450° C. while alternately feeding i) dry air, ii) moist air at relative humidities of 20, 50, and 80%, iii) dry air+20 ppm acetone, and iv) moist air at relative humidities of 20, 50, and 80%+20 ppm acetone. Acetone was previously mixed and its concentration was rapidly changed using a 4-way valve. The total gas flow rate was fixed to 100 SCCM such that no temperature difference was induced when the gas concentration was changed.

Example 1-2 and Comparative Example 1-2

0.15 M zinc nitrate hexahydrate ($Zn(NO_3)_2 \cdot 6H_2O$, 99.0%, Sigma-Aldrich, USA) and 0.1 M citric acid monohydrate ($HOC(COOH)(CH_2COOH)_2 \cdot H_2O$, 99.0%, Sigma-Aldrich, USA) were stirred in 600 mL of triple-distilled water for 30 min to prepare a spray solution. To the spray solution was added Ce nitrate hexahydrate ($Ce(NO_3)_3 \cdot 6H_2O$, 99.99%, Sigma-Aldrich, USA) in such an amount that the weight ratio of Ce to Zn was 5:95. After stirring for 5 min, the mixture was ultrasonically sprayed to form microdroplets. The microdroplets were instantaneously annealed while passing through a reaction furnace ($O_2$) at 900° C. at a flow rate of 10 L·min$^{-1}$, giving a ZnO hollow structure uniformly loaded with 5 wt % $CeO_2$ (Example 1-2). $CeO_2$-unloaded pristine ZnO having a hollow structure was synthesized in the same manner as described above, except that no Ce source was added (Comparative Example 1-2). Gas sensors were fabricated in the same manner as in Example 1-1.

Example 2-1 and Comparative Example 2-1

0.2 M tungsten oxide ($WO_3$, 99.9%, Sigma-Aldrich, USA) and 0.5 M sucrose ($C_{12}H_{22}O_{11}$, 99.5%, Sigma-Aldrich, USA) were added to a mixture of 540 mL of triple-distilled water and 60 mL of ammonium hydroxide solution ($NH_4OH$, 28.0-30.0%, Sigma-Aldrich, USA). The resulting mixture was stirred for 1 day to prepare a spray solution. To the spray solution was added Ce nitrate hexahydrate ($Ce(NO_3)_3 \cdot 6H_2O$, 99.99%, Sigma-Aldrich, USA) in such an amount that the weight ratio of Ce to W was 12:88. After stirring for 5 min, the mixture was ultrasonically sprayed to form microdroplets. The microdroplets were instantaneously annealed while passing through a reaction furnace ($O_2$) at 900° C. at a flow rate of 5 L·min$^{-1}$, giving a $WO_3$ yolk-shell structure uniformly loaded with 12 wt % $CeO_2$ (Example 2-1). $CeO_2$-unloaded pristine $WO_3$ having a yolk-shell structure was synthesized in the same manner as described above, except that no Ce source was added (Comparative Example 2-1). Gas sensors were fabricated in the same manner as in Example 1-1.

Example 2-2 and Comparative Example 2-2

0.2 M nickel nitrate hexahydrate ($Ni(NO_3)_2 \cdot 6H_2O$, 99.999%, Sigma-Aldrich, USA) and 0.7 M sucrose ($C_{12}H_{22}O_{11}$, 99.5%, Sigma-Aldrich, USA) were stirred in 600 mL of triple-distilled water for 30 min to prepare a spray solution. To the spray solution was added Ce nitrate hexahydrate ($Ce(NO_3)_3 \cdot 6H_2O$, 99.99%, Sigma-Aldrich, USA) in such an amount that the weight ratio of Ce to Ni was 30:70. After stirring for 5 min, the mixture was ultrasonically sprayed to form microdroplets. The microdroplets were instantaneously annealed while passing through a reaction furnace ($O_2$) at 900° C. at a flow rate of 5 L·min$^{-1}$, giving a NiO yolk-shell structure uniformly loaded with 30 wt % $CeO_2$ (Example 2-2). $CeO_2$-unloaded pristine NiO having a yolk-shell structure was synthesized in the same manner as described above, except that no Ce source was added (Comparative Example 2-2). Gas sensors were fabricated in the same manner as in Example 1-1.

Example 3 and Comparative Example 3

0.04 g of a commercial $SnO_2$ powder ($SnO_2$, %, Sigma-Aldrich, USA) was dispersed in 40 mL of triple-distilled water by sonication for 30 min to prepare a slurry. The slurry was stirred for 1 h. Thereafter, to the slurry was added Ce nitrate hexahydrate ($Ce(NO_3)_3 \cdot 6H_2O$, 99.99%, Sigma-Aldrich, USA) in such an amount that the weight ratio of Ce to Sn was 3:97. After stirring for 4 h, 10 mL of 2 g/L fresh sodium borohydride ($NaBH_4$, 99.99%, Sigma-Aldrich, USA) was rapidly injected into the slurry, stirred for additional 3 h, and washed five times with water by centrifugation. The remaining slurry was dried in an oven at 70° C. to obtain a $CeO_2$-loaded $SnO_2$ precursor. The precursor was annealed at 500° C. for 3 h, giving a fine powder of $SnO_2$ uniformly loaded with 3 wt % $CeO_2$ (Example 3). A fine powder of pristine $SnO_2$ was obtained by annealing a commercial $SnO_2$ fine powder at 500° C. for 3 h without the need for further processing (Comparative Example 3). Gas sensors were fabricated in the same manner as in Example 1-1.

Discussion

The gas sensing characteristics of the fabricated sensors were evaluated. As a result, the sensors of Example 1-1, Example 1-2, Example 2-1, Example 3, Comparative Example 1-1, Comparative Example 1-2, Comparative Example 2-1, and Comparative Example 3 were found to exhibit high resistances in air and low resistances as soon as acetone was fed, indicating their n-type semiconductor properties. The sensors of Example 2-2 and Comparative Example 2-2 were found to exhibit low resistances in air and high resistances as soon as acetone was fed, indicating their p-type semiconductor properties. The gas response of each n-type oxide semiconductor gas sensor was defined as $R_a/R_g$ ($R_a$: resistance of the sensor in air, $R_g$: resistance of the sensor in the gas) and the gas response of each p-type oxide semiconductor gas sensor was defined as $R_g/R_a$ ($R_a$ and $R_g$ are as defined above). The acetone sensing characteristics of each sensor were measured in a dry atmosphere and compared with the acetone responses and resistances of the sensor measured at relative humidities of 20, 50, and 80%. Detailed measurement methods are as follows.

300 sec after the resistance of each sensor in a dry atmosphere was kept constant, the atmosphere was suddenly changed to acetone (20 ppm) as an analyte gas. The sensor was exposed to the analyte gas for 300 sec. Thereafter, the atmosphere was again changed to a dry air atmosphere and maintained for 1100 sec. The gas response of the sensor was measured in the dry atmosphere. Thereafter, the atmosphere was suddenly changed to moist air at relative humidities of 20, 50, and 80% and maintained for 300 sec. Then, the sensor was exposed to the analyte gas and the moist air at relative humidities of 20, 50, and 80% for 300 sec. The gas sensing characteristics of the sensor at the first humidity were evaluated. The same procedure was repeated three times to measure changes in the gas sensing characteristics of the sensor as a function of the exposure time to moisture. The gas response variations (%) of the sensor were determined as values by dividing the gas responses at relative humidities of 20, 50, and 80% by the gas response in the dry atmosphere. The resistance variations (%) of the sensor were determined as values by dividing the resistances at relative humidities of 20, 50, and 80% by the resistance in the dry atmosphere. Hence, when the gas response variation and the resistance variation are all 100%, the humidity dependence of the sensor can be understood to be substantially negligible.

FIG. 4 shows SEM images of the fine powders synthesized based on ultrasonic spray pyrolysis in Comparative Example 1-1 (hollow pristine $SnO_2$, a), Comparative Example 1-2 (hollow pristine ZnO, c), Comparative Example 2-1 (yolk-shell $WO_3$, e), Comparative Example 2-2 (yolk-shell NiO, g), Example 1-1 (b), Example 1-2 (d), Example 2-1 (f), and Example 2-2 (h).

Referring to FIG. 4, the fine powders of Comparative Examples 1-1 and 1-2 were found to have hollow structures (a and c) and the fine powders of Comparative Examples 2-1 and 2-2 were found to have yolk-shell structures, each consisting of outer and inner hollow structures (e and g). The fine powders of Examples 1-1, 1-2, 2-1, and 22 were synthesized in the same manner, except that 2, 5, 12, and 30 wt % $CeO_2$ were loaded, respectively. The fine powders of Examples 1-1, 1-2, 2-1, and 22 maintained their hollow structures (b and d) and yolk-shell structures (f and h) irrespective of the loading and concentration of $CeO_2$.

FIG. 5 shows SEM images of the fine powder synthesized based on solution stirring in Example 3 (b) and the commercial $SnO_2$ fine powder (Comparative Example 3, a). Referring to FIG. 5, the commercial $SnO_2$ fine powder was as small as several nm (a) and the fine powder of Example 3 remained unchanged without size increase or aggregation even after $CeO_2$ loading (b).

FIG. 6 shows the results of XRD phase analysis for the fine powders of Example 1-1, Comparative Example 1-1, Example 1-2, Comparative Example 1-2, Example 2-1, Comparative Example 2-1, Example 2-2, and Comparative Example 2-2. Referring to FIG. 6, the X-ray diffraction pattern of the fine powder of Comparative Example 1-1 demonstrated that $SnO_2$ had a tetragonal structure (a1). In the X-ray diffraction pattern of the fine powder of Example 1-1 (a2), no peaks corresponding to $CeO_2$ were observed despite the loading of $CeO_2$ (2 wt %). This observation is believed to be because the amount of $CeO_2$ loaded is below the limit of detection of XRD or the $CeO_2$ nanoparticles were uniformly distributed over the entire surface of the $SnO_2$ hollow structure.

The diffraction pattern of the fine powder of Comparative Example 1-2 demonstrated that ZnO had a hexagonal structure (b1). As for the fine powder of Example 1-2, no peaks corresponding to (5 wt %) $CeO_2$ were observed despite the loading of $CeO_2$ above the limit of detection of XRD (b2). These results show that the loaded $CeO_2$ had a size of several nanometers and was very uniformly distributed over the entire surface of the ZnO hollow structure.

From the diffraction pattern of the fine powder of Comparative Example 2-1, $WO_3$ was confirmed to have a monoclinic structure (c1). The diffraction pattern of the fine powder loaded with 12 wt % of $CeO_2$ (Example 2-1) confirmed that $WO_3$ had a fluorite cubic structure. This structure is believed to be due to the absolutely large amount of $CeO_2$ (12 wt %) loaded irrespective of the degree of dispersion of the $CeO_2$ nanoparticles (c2). The fine powder of Example 2-1 showed a diffraction pattern of NiO having a cubic structure (d1) and the fine powder of Example 2-2 showed diffraction patterns of NiO and $CeO_2$ (d2).

In the results of phase analysis for each fine powder, no secondary phases between the corresponding gas sensing material ($SnO_2$, ZnO, $WO_3$ or NiO) and $CeO_2$ were observed. These results conclude that the loaded $CeO_2$ nanoparticles were uniformly distributed over the entire surface of the gas sensing material.

FIG. 7 shows the results of XRD phase analysis for the fine powders of Example 3 and Comparative Example 3. Referring to FIG. 7, the fine powder of Comparative Example 3 showed a diffraction pattern of $SnO_2$ having a tetragonal structure (a1). Although the same amount of $CeO_2$ (2 wt %) was loaded in the fine powders of Example 3 and Example 1-1, both a diffraction pattern of $SnO_2$ and a diffraction pattern of $CeO_2$ were found in the fine powder of Example 3 (a2), unlike in the fine powder of Example 1-1. These results show that $CeO_2$ nanoparticles were not uniformly distributed over the entire surface of the gas sensing material in the $CeO_2$-metal oxide nanostructure synthesized based on solution stirring compared to in the $CeO_2$-metal oxide nanostructure synthesized based on ultrasonic spray pyrolysis.

FIG. 8 compares the gas sensing transients and gas responses of the gas sensors fabricated in Comparative Example 1-1 and Example 1-1 to 20 ppm acetone in a dry atmosphere and at a relative humidity of 80%, which were measured at 450° C. Referring to FIG. 8, the gas sensor of Comparative Example 1-1 showed a high gas response to 20 ppm acetone in a dry atmosphere but underwent a considerable reduction in gas response when exposed to a relative humidity of 80%. The same results were also obtained in the resistance of the sensor (a1 and a2). This is a typical phenomenon when n-type oxide semiconductor (e.g., $SnO_2$) gas sensors are exposed to moisture and is a major cause of poor performance and malfunction of sensors. In contrast, even when suddenly exposed to a relative humidity of 80%, the gas sensor of Example 1-1 showed almost the same acetone response and resistance in a short time (<300 s) as those in the dry atmosphere (b1 of FIG. 8). These results clearly show that the loading of $CeO_2$ on $SnO_2$ can ensure constant gas sensing characteristics of the sensor with high reliability irrespective of the presence of external moisture (b2), unlike in general oxide semiconductor gas sensors.

FIG. 9 compares the gas responses of the gas sensors fabricated in Comparative Example 1-1, Example 1-1, Comparative Example 1-2, Example 1-2, Comparative Example 2-1, Example 2-1, Comparative Example 2-2, and Example 2-2 to 20 ppm acetone in a dry atmosphere and at relative humidities 20, 50, and 80%, which were measured at 450° C. Referring to FIG. 9, the gas response of each of the gas sensors of Comparative Examples 1-1, 1-2, 2-1, and 2-2 showed a tendency to gradually decrease because the degree of poisoning of the surface of the gas sensing material by hydroxyl groups increased with increasing the concentration of externally supplied moisture (a, c, e, and g). In contrast, the $CeO_2$-loaded gas sensors of Examples 1-1, 1-2, 2-1, and 2-2 showed almost the same gas response to acetone irrespective of the presence and concentration of moisture (b, d, f, and h). These results reveal that the loaded $CeO_2$ serves to prevent the surface of each gas sensing material from being poisoned by hydroxyl groups. The gas response variations of the sensors are indicative of the reliability of the sensor response. The gas response variations of the sensors of Comparative Examples 1-1, 1-2, 2-1, and 2-2 at a relative humidity of 80% were calculated to be 81%, 49%, 66%, and 84%, respectively, and those of the sensors of Examples 1-1, 1-2, 2-1, and 2-2 were calculated to be 103%, 97%, 98%, and 103%, respectively, which were close to 100%. These results clearly show that the loading of $CeO_2$ as a moisture absorbent on the humidity-dependent oxide semiconductors enables substantial removal of the humidity dependence of gas response.

FIG. 10 compares the resistances of the gas sensors of Comparative Example 1-1, Example 1-1, Comparative Example 1-2, Example 1-2, Comparative Example 2-1, Example 2-1, Comparative Example 2-2, and Example 2-2 in a dry atmosphere and at relative humidities of 20, 50, and 80%, which were measured at 450° C. Referring to FIG. 10, the resistances of the gas sensors of Comparative Examples 1-1, 1-2, and 2-1, which were fabricated using the n-type oxide semiconductors, decreased with increasing relative humidity (a, c, and e). The decreased resistances of the gas sensors are explained by an increase in the amount of electrons created by the reaction between moisture and the gas sensing materials. In contrast, the resistance of the gas sensor of Comparative Example 2-1, which was fabricated using the p-type oxide semiconductor, gradually increased with increasing relative humidity (g) because the concentration of holes in NiO was reduced by electrons created as a result of the reaction with moisture. The humidity-dependent changes in the resistance of the comparative gas sensors showed a similar tendency to resistance changes caused by the reaction of the sensors with a gas (n-type: resistance decrease when the gas was sensed; p-type: resistance increase when the gas was sensed), which is a major cause of malfunction of the sensors. In contrast, the inventive $CeO_2$-loaded gas sensors showed substantially the same resistances irrespective of the presence and concentration of external moisture (b, c, f, and h). The gas resistance variations of the sensors are indicative of the reliability of the sensors. The gas resistance variation of each sensor was defined as the ratio of the resistance in a dry atmosphere to the resistance in a moist atmosphere. The gas resistance variations of the comparative sensors at a relative humidity of 80% were calculated to be 61% (Comparative Example 1-1), 46% (Comparative Example 1-2), 73% (Comparative Example 2-1), and 93% (Comparative Example 2-2), and those of the inventive sensors were calculated to be 97% (Example 1-1), 99% (Example 1-2), 100% (Example 2-1), and 100% (Example 2-2), which were close to 100%. These results clearly show that the loading of $CeO_2$ nanoparticles as moisture absorbents on the gas sensing materials can ensure high gas response of the gas sensors, good resistance stability of the gas sensors against moisture, and constant gas sensing characteristics of the gas sensors with high reliability irrespective of the presence and concentration of moisture.

FIG. 11 compares the gas responses of the gas sensors of Comparative Example 3 and Example 3 to 20 ppm acetone in a dry atmosphere and at relative humidities of 20, 50, and 80%, which were measured at 450° C. Referring to FIG. 11, there were significant differences in the acetone response and resistance of the gas sensor using the commercial $SnO_2$ powder (Comparative Example 3) between in a dry atmosphere and at a relative humidity of 80% (gas response variation: 84% (a) resistance variation: 75% (c))). The $CeO_2$-loaded gas sensor fabricated including solution stirring (Example 3) showed less humidity-dependent acetone response and resistance (gas response variation: 89% (b) and resistance variation: 93% (d)) than the gas sensor of Comparative Example 3 but did not provide reliability against moisture comparable to that of the gas sensor of Example 1-1 (gas response variation: 103%; sensor resistance variation: 97%) despite the same amount of Ce loaded. These results show that the loading of $CeO_2$ on the oxide semiconductor is sufficient to reduce the humidity dependence of the sensor, and at the same time, uniform coating of $CeO_2$ over the entire surface of the gas sensing material is of great importance in maximizing the effect of $CeO_2$ on the absorption and removal of moisture.

Example 4: Fabrication of Gas Sensors Including $CeO_2$ Nanoparticles Uniformly Coated on the Surface of $In_2O_3$ Hollow Structure (Including Layer-by-Layer Process)

0.05 M In (III) nitrate hydrate ($In(NO_3)_3 \cdot xH_2O$, 99.999%, Sigma-Aldrich, USA) (x=2, 6 or 9) and 0.15 M sucrose ($C_{12}H_{22}O_{11}$, 99.5%, Sigma-Aldrich, USA) were stirred in 600 mL of triple-distilled water for 30 min, followed by ultrasonic spray. The resulting microdroplets were instantaneously annealed while passing through a reaction furnace ($O_2$) at 900° C. at a flow rate of 5 L/min, giving a fine powder of an $In_2O_3$ hollow structure. The fine powder (0.04 g) was dispersed in 50 mL of triple-distilled water by sonication for 5 min, and then 20 mL of a mixture of aqueous ammonia/hydrogen peroxide solution (1:1) was added thereto. The resulting solution was stirred at 80° C. for 30 min to clean the $In_2O_3$ surface. After washing five times with water by centrifugation, the remaining fine powder was mixed with 20 mL of a solution (0.5 g/L) of polyethyleneimine (PEI, $H(NHCH_2CH_2)_nNH_2$, Mw: ~25,000, Sigma-Aldrich, USA). The mixture was stirred for 3 h to modify the $In_2O_3$ surface with positive charges. The excess PEI was washed away five times with water by centrifugation and the remaining fine powder was mixed with 20 mL of a solution (0.5 g/L) of polyacrylic acid (PAA, $(C_3H_4O_2)_n$, Mv: ~450,000, Sigma-Aldrich, USA). The mixture was stirred for 2 h to modify the $In_2O_3$ surface with negative charges. The excess PAA was washed away five times with water by centrifugation and the remaining fine powder was dispersed in 40 mL of triple-distilled water. To the dispersion was added 2.9 wt % (Example 4-2), 5.7 wt % (Example 4-1), 10.7 wt % (Example 4-3) or 19.4 wt % (Example 4-4) of Ce (III) nitrate hexahydrate ($Ce(NO_3)_3 \cdot 6H_2O$, 99.99%, Sigma-Aldrich, USA). Stirring was continued for 3 h to induce electrostatic bonding of Ce ions and the surface charges of $In_2O_3$. After stirring for 3 h, 10 mL of 2 g/L fresh sodium borohydride ($NaBH_4$, 99.99%, Sigma-Aldrich, USA) was rapidly injected. Stirring was continued for additional 3 h to reduce Ce ions electrostatically bonded to the $In_2O_3$ surface to $CeO_2$. After washing five times with water by centrifugation, the remaining slurry was dried in an oven at 70° C. for 2 days to obtain a fine powder of $CeO_2$-coated $In_2O_3$. The fine powder was annealed at 500° C. for 3 h, giving a fine powder in which 4.97 wt % (Example 4-2), 11.7 wt % (Example 4-1), 22.4 wt % (Example 4-3) or 39.9 wt % (Example 4-4) of $CeO_2$ nanoparticles were uniformly coated on the surface of the $In_2O_3$ hollow structure. The fine powder was mixed with triple-distilled water, drop coated on an alumina substrate where an Au electrode was disposed, and annealed at 500° C. for 2 h to fabricate a gas sensor. Changes in the resistance of the sensor were measured at 450° C. while alternately feeding air in a dry atmosphere and moist air at relative humidities of 20, 50, and 80% or air in a dry atmosphere+gas mixture and moist air at relative humidities of 20, 50, and 80%+gas mixture. An analyte gas was previously mixed and its concentration was rapidly changed using a 4-way valve. The total gas flow rate was fixed to 100 SCCM such that no temperature difference was induced when the gas concentration was changed.

Example 5: Fabrication of Inventive Gas Sensor Including CeO$_2$ Nanoparticles Uniformly Coated on the Surface of In$_2$O$_3$ Hollow Structure (Including Preparing Composite for Gas Detection Based on Batch Process)

0.05 M indium (III) nitrate hydrate (In(NO$_3$)$_3$.xH$_2$O, 99.999%, Sigma-Aldrich, USA) and 0.15 M sucrose (C$_{12}$H$_{22}$O$_{11}$, 99.5%, Sigma-Aldrich, USA) were stirred in 600 ml of triple-distilled water for 30 min to prepare a spray solution. To the spray solution was added Ce (III) nitrate hexahydrate (Ce(NO$_3$)$_3$.6H$_2$O, 99.99%, Sigma-Aldrich, USA) in such an amount that the weight ratio of Ce to In was 5.7:94.3. After stirring for 5 min, the mixture was ultrasonically sprayed to form microdroplets. The microdroplets were instantaneously annealed while passing through a reaction furnace (O$_2$) at 900° C. at a flow rate of 5 L/min, giving an In$_2$O$_3$ hollow structure uniformly loaded with 5.7 wt % CeO$_2$. Thereafter, a gas sensor was fabricated and its gas sensing characteristics were measured in the same manner as in Example 4.

Comparative Example 4: Fabrication of Gas Sensor Including In$_2$O$_3$ Hollow Structure (Unloaded with CeO$_2$)

0.05 M Indium (III) nitrate hydrate (In(NO$_3$)$_3$.xH$_2$O, 99.999%, Sigma-Aldrich, USA) and 0.15 M sucrose (C$_{12}$H$_{22}$O$_{11}$, 99.5%, Sigma-Aldrich, USA) were stirred in 600 ml of triple-distilled water for 30 min, followed by ultrasonic spray. The resulting microdroplets were instantaneously annealed while passing through a reaction furnace (O$_2$) at 900° C. at a flow rate of 5 L/min, giving an In$_2$O$_3$ hollow structure. Thereafter, a gas sensor was fabricated and its gas sensing characteristics were measured in the same manner as in Example 4.

Comparative Example 5: Fabrication of Gas Sensors Including Small Amount or Excess CeO$_2$ Nanoparticles Coated on the Surface of In$_2$O$_3$ Hollow Structure 0.05 M In (III) nitrate hydrate (In(NO$_3$)$_3$.xH$_2$O, 99.999%, Sigma-Aldrich, USA) and 0.15 M sucrose (C$_{12}$H$_{22}$O$_{11}$, 99.5%, Sigma-Aldrich, USA) were stirred in 600 ml of triple-distilled water for 30 min, followed by ultrasonic spray. The resulting microdroplets were instantaneously annealed while passing through a reaction furnace (O$_2$) at 900° C. at a flow rate of 5 L/min, giving a fine powder of an In$_2$O$_3$ hollow structure. The fine powder (0.04 g) was dispersed in 50 mL of triple-distilled water by sonication for 5 min, and then 20 mL of a mixture of aqueous ammonia/hydrogen peroxide solution (1:1) was added thereto. The resulting solution was stirred at 80° C. for 30 min to clean the In$_2$O$_3$ surface. After washing five times with water by centrifugation, the remaining fine powder was mixed with 20 mL of a solution (0.5 g/L) of polyethyleneimine (PEI, H(NHCH$_2$CH$_2$)$_n$NH$_2$, Mw: ~25,000, Sigma-Aldrich, USA). The mixture was stirred for 3 h to modify the In$_2$O$_3$ surface with positive charges. The excess PEI was washed away five times with water by centrifugation and the remaining fine powder was mixed with 20 mL of a solution (0.5 g/L) of polyacrylic acid (PAA, (C$_3$H$_4$O$_2$)$_n$, Mv: ~450,000, Sigma-Aldrich, USA). The mixture was stirred for 2 h to modify the In$_2$O$_3$ surface with negative charges. The excess PAA was washed away five times with water by centrifugation and the remaining fine powder was dispersed in 40 mL of triple-distilled water. To the dispersion was added 0.3 wt % (Comparative Example 5-1), 1.2 wt % (Comparative Example 5-2), 32.4 wt % (Comparative Example 5-3) or 49.0 wt % (Comparative Example 5-4) of Ce (III) nitrate hexahydrate (Ce(NO$_3$)$_3$.6H$_2$O, 99.99%, Sigma-Aldrich, USA). Stirring was continued for 3 h to induce electrostatic bonding of Ce ions and the surface charges of In$_2$O$_3$. After stirring for 3 h, 10 mL of 2 g/L fresh sodium borohydride (NaBH$_4$, 99.99%, Sigma-Aldrich, USA) was rapidly injected. Stirring was continued for additional 3 h to reduce Ce ions electrostatically bonded to the In$_2$O$_3$ surface to CeO$_2$. After washing five times with water by centrifugation, the remaining slurry was dried in an oven at 70° C. to obtain a fine powder of CeO$_2$-coated In$_2$O$_3$. The fine powder was annealed at 500° C. for 3 h, giving a fine powder in which 1.04 wt % (Comparative Example 5-1), 2.33 wt % (Comparative Example 5-2), 45.6 wt % (Comparative Example 5-3), and 55.0 wt % (Comparative Example 5-4) of CeO$_2$ nanoparticles were uniformly coated on the surface of the In$_2$O$_3$ hollow structure. Thereafter, a gas sensor was fabricated and its gas sensing characteristics were measured in the same manner as in Example 4.

The sensors thus fabricated showed high resistances in air irrespective of the presence and concentration (RH20, 50, 80%) of moisture and reduced resistances as soon as a reducing gas was fed, indicating their n-type semiconductor properties. The gas response of each gas sensor was defined as $R_a/R_g$ ($R_a$: resistance of the sensor in air, $R_g$: resistance of the sensor in the gas). The sensing characteristics of each sensor for acetone, carbon monoxide, ammonia, and toluene were measured in a dry atmosphere and at relative humidities of 20, 50, and 80%. The selectivities of each sensor for acetone were calculated by comparing the response of the sensor to acetone with those of the sensor to other gases.

After the resistance of the sensor was kept constant in a dry air atmosphere, the atmosphere was suddenly changed to air including a predetermined concentration of the analyte gas. The sensor was exposed to the analyte gas for 300 sec. Thereafter, the atmosphere was again changed to a dry air atmosphere and maintained for 1100 sec. The gas response of the sensor was measured in the dry atmosphere. Thereafter, the atmosphere was suddenly changed to moist air at relative humidities of 20, 50, and 80% and maintained for 300 sec. Then, the sensor was exposed to the analyte gas and the moist air at relative humidities of 20, 50, and 80% for 300 sec. The gas sensing characteristics of the sensor at the first humidity were evaluated. The same procedure was repeated three times to measure changes in the gas sensing characteristics of the sensor as a function of the exposure time to moisture. The gas response variations (%) of the sensor were determined as values by dividing the gas responses at relative humidities of 20, 50, and 80% by the gas response in the dry atmosphere and multiplying the results by 100. The resistance variations (%) of the sensor were determined as values by dividing the resistances at relative humidities of 20, 50, and 80% by the resistance in the dry atmosphere and multiplying the results by 100. Hence, when the gas response variation and the resistance variation are all 100%, the humidity dependence of the sensor can be understood to be substantially negligible.

Discussion

FIGS. 14a to 14i are SEM images of the composites for gas detection synthesized based on ultrasonic spray pyrolysis and the subsequent layer-by-layer process. The composites of Example 4 (14d, 14e, 14f, and 14g), Comparative Example 4 (14a), and Comparative Example 5 (14b, 14c, 14h, and 14i) were confirmed to maintain their hollow structures regardless of the amount of Ce loaded. In contrast, in the SEM images of the composites of Comparative Example 5-3 (FIG. 14h) and Comparative Example 5-4 (FIG. 14i), a number of $CeO_2$ planar and cubic structures as well as the Ce-coated $In_2O_3$ hollow structure were observed. This observation is believed to be because too large an amount of Ce was loaded, with the result that all $CeO_2$ nanoparticles were not formed on the surface of the $In_2O_3$ hollow structure and some of them aggregated and underwent self-assembly.

FIGS. 15 and 16 are TEM images of the composites for gas detection prepared in Comparative Example 4 (FIGS. 15a to 15c), Example 4-1 (FIGS. 15d to 15g), Example 4-3 (FIGS. 16a to 16d), and Example 4-4 (FIGS. 16e to 16h). The shells of the $In_2O_3$ hollow structures were ~15 nm in thickness regardless of the amount of Ce loaded. Componential analysis through elemental mapping revealed that the loaded Ce was uniformly distributed on the $In_2O_3$ surfaces without aggregation (FIGS. 15g, 16d, and 16h).

FIGS. 17a to 17d are SEM and TEM images of the composite for gas detection synthesized based on a batch process instead of a layer-by-layer process in Example 5. The $CeO_2$ nanoparticles were not present only on the $In_2O_3$ surface of the composite but were uniformly distributed over the entire region of the $In_2O_3$ hollow structure, as revealed by elemental mapping (FIG. 17d), unlike in the fine powders synthesized based on a layer-by-layer process.

FIG. 18 shows the results of X-ray phase analysis for the composites for gas detection prepared in Comparative Example 4, Example 4, and Comparative Example 5. From the diffraction patterns of the composites of Example 4-3 (f-1, f-2, and f-3), Example 4-4 (g-1, g-2, and g-3), Comparative Example 5-3 (h-1, h-2, and h-3), and Comparative Example 5-4 (i-1, i-2, and i-3), it can be confirmed that $CeO_2$ nanoparticles formed on the $In_2O_3$ surfaces had fluorite cubic structures. In contrast, peaks attributed to $CeO_2$ were not observed in the composites of Comparative Example 4 (a-1, a-2, and a-3), Comparative Example 5-1 (b-1, b-2, and b-3), Comparative Example 5-2 (c-1, c-2, and c-3), Example 4-2 (d-1, d-2, and d-3), and Example 4-1 (e-1, e-2, and e-3). These results are partially due to the limit of detection of XRD but are believed to be because $Ce^{4+}$ of $CeO_2$ was reduced by electrons received from $In_2O_3$, with the result that a large amount of $Ce^{3+}$ was present, leading to poor crystallinity of $CeO_2$. Thus, Ce 3d spectra measured by XPS were separated by peak fitting to calculate the amount of $Ce^{3+}$. As a result, as the amount of Ce loaded increased, the ratio of $Ce^{3+}$ to $Ce^{4+}$ decreased from ~40% (Comparative Example 5-1) to ~20% (Comparative Example 5-4) (see FIG. 19), which indicates that the number of oxygen vacancies per $CeO_2$ nanoparticle decreased with increasing amount of Ce loaded and thus the number of oxygen ions to be adsorbed was reduced, deteriorating the ability to transition between $Ce^{3+}$ and $Ce^{4+}$. As a result of analysis of the In 3d spectra, no shifts of In 3d peaks were found in all spectra regardless of the amount of Ce loaded, which is believed to be because the ionic radius of $Ce^{3+}$ or $Ce^{4+}$ is very different from that of $In^{3+}$, making it impossible for $Ce^{3+}$ or $Ce^{4+}$ to be incorporated into the $In_2O_3$ lattice through substitution. This means that when the coated $CeO_2$ nanoparticles are discretely present, the Ce loading-dependent change in the resistance of the sensor is entirely dependent on the migration of electrons between $In_2O_3$ and $CeO_2$.

FIGS. 20a and 20b show changes in the resistance and gas response of the sensors of Example 4-1 (FIG. 20a) and Comparative Example 4 (FIG. 20b) to various gases in a dry atmosphere and at a relative humidity of 80%, which were measured at a sensing temperature of 450° C. The resistances of the sensor of Example 4-1 in a dry atmosphere (7.72 Me) and relative humidities of 20% (7.34 Me), 50% (7.43 Me), and 80% (7.45 Me) were substantially constant (see FIG. 21b). In contrast, the sensor of Comparative Example 4 in a dry atmosphere and relative humidities of 20%, 50%, and 80% had resistances of 0, 7.45, 5.85, and 5.41 kΩ, respectively, which were greatly dependent on the humidity (see the left panel of FIG. 21b). This demonstrates that the loading of $CeO_2$ can remove the humidity dependence of the sensor resistance. The gas responses of the sensor of Example 4-1 to 20 ppm acetone, 20 ppm ethanol, 200 ppm hydrogen, 200 ppm carbon monoxide, 200 ppm ammonia, 100 ppm toluene, and 50 ppm formaldehyde at a humidity of 80% were 93-96% of those in a dry state (FIG. 20a). These results conclude that the gas response of the sensor was not substantially affected by changes in humidity. In contrast, the gas responses of the sensor of Comparative Example 4 to the same gases at a humidity of 80% were 21-42% of those in a dry state (FIG. 20b). These results conclude that the gas response of the sensor was significantly reduced to $\frac{1}{5}$-$\frac{1}{3}$ depending on the presence of moisture.

It is very difficult to determine a point of reference for gas response measurement when the resistance of a gas sensor varies depending on humidity. It is also difficult to determine the concentration of a gas when the gas response of a sensor greatly varies depending on humidity. In conclusion, little influence of humidity on the resistance and gas response of a sensor indicates that the concentration of a gas can be quantitatively determined regardless of changes in humidity. Herein, the loading of $CeO_2$ enables the fabrication of a gas sensor independent of moisture.

FIGS. 21a to 21d show the gas responses of the composites for gas detection prepared in Comparative Example 4, Comparative Example 5-1, Comparative Example 5-2, Example 4-2, Example 4-1, Example 4-3, and Example 4-4 to 20 ppm acetone in a dry atmosphere and at relative humidities of 20%, 50%, and 80%, which were measured at an operating temperature of 450° C. (FIG. 21a), and resistances (FIG. 21b), humidity-dependent gas response variations (FIG. 21c) and resistance variations (21d) of the composites. As for the gas sensors of Comparative Example 5-3 and Comparative Example 5-4, it was difficult to obtain reproducible results in terms of sensing characteristics, which is believed to be due to the random presence of $CeO_2$ planar and cubic structures as well as $CeO_2$-coated $In_2O_3$ hollow structures in the slurries. The gas response of the gas sensor of Comparative Example 4 to acetone 200 ppm was as high as 22.2 in a dry atmosphere but it decreased until the amount of Ce loaded reached 2.33 wt %, increased slightly when the amount of Ce loaded was in the range of 2.33-11.7 wt %, and decreased slightly or was almost the same when the amount of Ce loaded was in the range of 11.7-39.9 wt % (see FIG. 21a). This tendency is associated with the reaction/recovery rates of a sensor. In contrast, the resistance of the gas sensor of Comparative Example 4 increased until the amount of Ce loaded increased to 11.7 wt %, and thereafter, it decreased slightly or was almost the same (see FIG. 21b). This means that electrons were substantially depleted from the $In_2O_3$ hollow structure when 11.7 wt % of Ce was loaded and that the excess (>11.7 wt %) of $CeO_2$ could not bring electrons from $In_2O_3$. The inventive sensors can be relatively easily fabricated due to their low resistances (0.5-10 Me). The resistances of the sensors can be further reduced to the level of 0.05-1 Me through control over the intervals of the sensors. The gas responses of the composite of Comparative Example 4 at relative humidities of 20, 50, and 80% were 7.33, 5.41, and 4.76, respectively, which were much lower than the gas response in a dry atmosphere (22.2). These results demonstrate the humidity dependence of the composite (see the left panel of FIG. 21a). Humidity-dependent gas response variations (%) of the sensor of Comparative Example 4 were calculated to quantify the humidity dependence of the sensor. As a result, the gas response variations of the sensor were 36.6, 24.7, and 20.7 at relative humidities of 20%, 50%, and 80%, respectively, showing a tendency to gradually decrease with increasing relative humidity (see the left panel of FIG. 21c). The sensor of Comparative Example 4 showed very different gas responses in dry and moist atmospheres, and at the same time, its gas responses varied greatly depending on the concentration of moisture. The sensor of Comparative Example 4 clearly shows the problems of general oxide semiconductor gas sensors. The gas response variations of the sensor increased remarkably (>100%) when the amount of Ce loaded increased, and thereafter, it gradually decreased to 97.9, 96.7, and 96.3 at relative humidities of 20%, 50%, and 80%, which are close to 100% (FIG. 21c). The humidity-dependent resistance variation (%) of a sensor is an important factor determining the humidity stability of the sensor. The humidity-dependent resistance variations of the sensor of Comparative Example 4 were 46.7, 35.4, and 31.6 at relative humidities of 20%, 50%, and 80%, respectively. That is, the resistance variation of the sensor showed a tendency to decrease with increasing relative humidity. In contrast, the resistance variation of the sensor gradually increased with increasing amount of Ce loaded. When 11.7 wt % of Ce was loaded, the resistance variations of the sensor at relative humidities of 20%, 50%, and 80% were 95.0, 96.3, and 96.5, respectively, which were close to 100 (FIG. 21d). These results show that the gas response of the $In_2O_3$ hollow structure loaded with 11.7 wt % of Ce to acetone was almost constant irrespective of the presence and concentration of moisture.

FIGS. 22a and 22b show changes in the 90% gas response rate and 90% recovery rate of the sensors depending on the amount of Ce loaded. The sensors showed high 90% response rates of few seconds regardless of the amount of Ce loaded (FIG. 22a). In contrast, the 90% recovery rates of the sensors greatly increased until the amount of Ce loaded reached 2.33 wt %, and thereafter, it tended to decrease gradually (FIG. 22b). The recovery mechanism of a sensor is based on the resorption of oxygen in air to the sensing material and is thus directly associated with the ability of the sensing material to adsorb oxygen. That is, the highest recovery rate of the $In_2O_3$ sensor loaded with 2.33 wt % of Ce suggests that the sensor had a better ability to adsorb oxygen than any other sensor. XPS analysis revealed that the ratio of $Ce^{3+}/Ce^{4+}$ in $CeO_2$ showed a tendency to decrease with increasing amount of Ce loaded (FIG. 19), indicating that the ability of $CeO_2$ nanoparticles to adsorb oxygen decreases with increasing amount of Ce loaded in view of the mechanism of oxygen adsorption of $CeO_2$ using oxygen vacancies. However, the absolute amount of $Ce^{3+}$ will gradually increase with increasing amount of Ce loaded, which explains why the ability of $CeO_2$ to adsorb oxygen gradually increased until the amount of Ce loaded reached 2.33 wt %, and thereafter, it began to decrease. The recoverability of the sensor is closely related to the lowest gas response of $In_2O_3$ loaded with 2.33 wt % of Ce (FIG. 21a). Since oxygen is thermodynamically adsorbed to $CeO_2$ in preference to reducing gases, the good ability of $In_2O_3$ loaded with 2.33 wt % of Ce to adsorb oxygen is responsible for its low gas response. Despite the good ability of $In_2O_3$ loaded with 2.33 wt % of Ce to adsorb oxygen, the resistance of the sensor in a moist atmosphere was very different from that in a dry atmosphere (FIGS. 21b and 21d). This is believed to be because the small amount of Ce loaded failed to effectively protect a large portion of the surface of the main sensing material $In_2O_3$. The resistance variation of the sensor approximated almost 100% when 11.7 wt % of Ce was loaded. Therefore, the amount of $CeO_2$ nanoparticles is preferably adjusted to ≥11.7 wt % in order to protect a large portion of the surface of $In_2O_3$ against moisture.

FIGS. 23a and 23b show the gas sensing transients and gas responses of the gas sensors of Comparative Example 4 (FIG. 23a) and Example 4-1 (FIG. 23b) in a dry atmosphere and at a relative humidity of 80% to 20 ppm acetone. The gas response and resistance of the gas sensor of Comparative Example 4 in a dry atmosphere were largely different from those at a relative humidity of 80% (FIG. 23a). In contrast, there were no substantial changes in the gas response and resistance of the gas sensor of Example 4-1 in a dry atmosphere and at a relative humidity of 80% (FIG. 23b). These results show that only when $CeO_2$ nanoparticles are uniformly distributed on the surface of the $In_2O_3$ hollow structure can the surface of the main sensing material $In_2O_3$ be effectively protected against moisture entering from the outside, ensuring constant gas response and resistance of the sensor irrespective of the presence and concentration of moisture.

FIGS. 24a and 24b show the gas sensing transients of the gas sensors of Comparative Example 4 (FIG. 24a) and Example 4-1 (FIG. 24b) to 20 ppm acetone in a dry atmosphere and at relative humidities of 20%, 50%, and 80% and changes in the resistance and gas response of the sensors in a dry atmosphere and at relative humidities of 20%, 50%, and 80% as a function of the number of measurements. The gas responses and resistances of the sensor of Comparative Example 4 at the relative humidities were significantly different from those in a dry atmosphere (FIG. 24a). In contrast, the gas responses and resistances of the sensor including the $In_2O_3$ hollow structure coated with 11.7 wt % of Ce in a dry atmosphere were close to those at the relative humidities in a very short time (<300 s) irrespective of the concentration of moisture (FIG. 24b). This clearly shows that the sensor of Example 4-1 can detect acetone with almost constant gas response in a very short time irrespective of the presence and concentration of moisture.

FIGS. 25a and 25b show the gas responses and selectivities of the gas sensors of Comparative Example 4 (FIG. 25a) and Example 4-1 (FIG. 25b) to 20 ppm acetone over other noise gases in a dry atmosphere and at a relative humidity of 80%. In this experiment, the gas sensing characteristics of the gas sensors were investigated to determine whether the exhaled breath of patients with diabetes is applicable to the diagnosis of disease. The gas sensing characteristics were measured from non-drunken patients to exclude the gas response to ethanol. Other possible biomarker gases from patients were considered as noise gases. The sensor of Comparative Example 4 showed a high selectivity of ≥3 for acetone in a dry atmosphere (FIG. 25a). Although the gas response of the sensor of Example 4-1 was reduced by the loading of Ce, the selectivity of the sensor for acetone was still as high as ≥3 (FIG. 25b). This is believed to be because $CeO_2$ is a well-known basic catalyst to promote selective sensing to the acidic gas acetone. The selectivity of the sensor of Comparative Example 4 for acetone at a relative humidity of 80% was reduced to 1.78 (FIG. 25a). In contrast, the selectivity of the sensor of Example 4-1 for acetone at a relative humidity of 80% was 3.54, which was almost the same as that in a dry atmosphere (3.43) (FIG. 25b). This phenomenon was observed because $CeO_2$ nanoparticles coated on the surface of $In_2O_3$ protected the main sensing material $In_2O_3$ against moisture and thus loss of oxygen ions by moisture was prevented, causing no changes in the gas sensing characteristics of the sensor in dry and moist atmospheres. Therefore, the experimental results clearly reveal that the sensor of Example 4-1 can selectively detect acetone with high gas response irrespective of presence and concentration of moisture.

FIGS. 26a and 26b show the transients and gas responses of the gas sensors of Example 4-1 to different concentrations of acetone gas in a dry atmosphere and at a relative humidity of 80%. The gas responses of the gas sensor of Example 4-1 to different concentrations of acetone in a dry atmosphere and at a relative humidity of 80% were different, but the gas responses and resistances of the sensor were constant irrespective of the presence of moisture (FIG. 26a). This clearly shows that the gas sensor of Example 4-1 can detect the gas in air in real time irrespective of the presence and concentration of moisture. Acetone is an environmental pollution gas and is a biomarker gas that is detected in different amounts in the exhaled breaths of healthy subjects (300-900 ppb) and patients suffering with diabetes (≥1800 ppb). A sensor capable of selectively detecting around 1 ppm acetone irrespective of the presence and concentration of moisture can be applied to the self-diagnosis of diabetes. The sensor of Example 4-1 had a limit of detection of at least 500 ppb for acetone (FIG. 26b). Therefore, it is expected that the gas sensor of Example 4-1 will be sufficiently utilized for the diagnosis of diseases, such as self-diagnosis of diabetes from the amount of acetone detected in the exhaled breath of patients.

FIG. 27 shows the gas sensing transients of the gas sensor of Example 5 to 20 ppm acetone in a dry atmosphere and at a relative humidity of 80%. The gas sensor including $In_2O_3$ loaded with 5.7 wt % of Ce synthesized based on a batch process showed no significant difference in gas sensing characteristics in dry and moist atmospheres. This clearly shows that the sensor could detect a target gas with high selectivity and its gas response and resistance reached constant levels in a very short time when above a predetermined amount of $CeO_2$ was uniformly loaded on $In_2O_3$ regardless of how the gas sensing material was synthesized.

INDUSTRIAL APPLICABILITY

The composite for gas detection and the gas sensor including the composite as a material for a gas sensing layer according to the present invention can rapidly detect an analyte gas with high gas response irrespective of the presence and concentration of moisture. Due to these advantages, the composite and the gas sensor of the present invention are useful in a wide range of applications, including measurement of drivers' blood alcohol levels, detection of explosive gases, detection of exhaust gases, and detection of harmful gases. In addition, the gas sensor of the present invention is suitable for use as a gas sensor for the detection of an indoor/outdoor environmental gas, a gas sensor for self-diagnosis of disease or an artificial olfactory sensor.

The invention claimed is:

1. A method for preparing a composite for gas detection, comprising:
    a) preparing a solution comprising an In salt and a sugar;
    b) subjecting the solution to spray pyrolysis forming an $In_2O_3$ hollow structure spray pyrolysis product;
    c) adding surface charge modifiers to the spray pyrolysis product to obtain a powder in which charges have been introduced on the surface of the $In_2O_3$ hollow structure;
    d) mixing a dispersion of the powder with a Ce salt solution to prepare a mixture solution; and
    e) adding a reducing agent to the mixture solution to form a reduced product, followed by washing, drying and collecting the reduced product to obtain a fine powder in which $CeO_2$ nanoparticles are dispersed on the surface of the $In_2O_3$ hollow structure.

2. The method according to claim 1, wherein the In salt is selected from the group consisting of $In(NO_3)_3.xH_2O$ (x=2, 6 or 9) and mixtures thereof the Ce salt is selected from the group consisting of $Ce(NO_3)_3.6H_2O$, $Ce(SO_4)_2.4H_2O$, $CeCl_3.4H_2O$, and mixtures thereof and the sugar is selected from the group consisting of sucrose, glucose, and mixtures thereof.

3. The method according to claim 1, wherein, in step b), the spray pyrolysis is performed by spraying the solution into an electric furnace heated to 600° C. to 1100° C. at a rate of 2 L/m to 50 L/m.

4. The method according to claim 1, wherein in step c) the charges are introduced by sequentially adding a surface positive charge modifier and a surface negative charge modifier.

5. The method according to claim 4, wherein the surface positive charge modifier is selected from the group consisting of polyethyleneimine, poly(allylamine hydrochloride), poly(diallyldimethylammonium chloride), and mixtures thereof.

6. The method according to claim 4, wherein the surface negative charge modifier is selected from the group consisting of polyacrylic acid, poly(styrenesulfonate), poly(vinylsulfonate), and mixtures thereof.

* * * * *